United States Patent [19]

Auerswald et al.

[11] Patent Number: 5,118,668
[45] Date of Patent: Jun. 2, 1992

[54] VARIANTS OF BOVINE PANCREATIC TRYPSIN INHIBITOR AND PHARMACEUTICAL USE THEREOF

[75] Inventors: Ernst-August Auerswald, Munich; Wolfgang Bruns, Wuppertal; Dietrich Hörlein, Wuppertal; Gerd Reinhardt, Wuppertal; Eugen Schnabel, Wuppertal; Werner Schröder, Wuppertal, all of Fed. Rep. of Germany

[73] Assignee: Bayer Aktiengesellschaft, Leverkusen, Fed. Rep. of Germany

[21] Appl. No.: 221,835

[22] Filed: Jul. 20, 1988

[30] Foreign Application Priority Data

Aug. 7, 1987 [GB] United Kingdom ............... 8718777

[51] Int. Cl.⁵ ............................................. C07K 7/10
[52] U.S. Cl. ........................... 514/12; 530/324; 435/69.2
[58] Field of Search .............. 530/324; 435/69.2; 514/12

[56] References Cited

FOREIGN PATENT DOCUMENTS 0132732 2/1985 European Pat. Off.
0297362 1/1989 European Pat. Off.
0339942 11/1989 European Pat. Off.

OTHER PUBLICATIONS

Wunderer et al. 1981. Methods in Enzymology 80:816-820.
Wachter et al. 1980. Febs. Lett. 119(1):58-62.
Kato, I. 1979. Fed. Proc. 38:832, Abstract No. 3168.
Hochstrasser et al. 1985. Biol. Chem. Hoppe-Seyler vol. 366:473-478.
Strydom et al. 1981. Hoppe-Seyler's Physiol. Chem. 362:1377-1384.
Kingston et al. 1986. Biochem. J. 233-443-450.
Bowie et al. 1990. Science 247:1306-1310.
Dayhoff et al. 1972. Atlas of Protein Sequence and Structure 5:89-99.
Tschesche et al. 1983. Adv. Exp. Med. Biol. 156A:3-29-337.
Tschesche et al. 1987. Biochimica et Biophysica Acta 913:97-101.
Biochemistry, vol. 16, No. 8, Apr. 19, 1977, pp. 1531-1541, Tan et al., Synthesis and characterization of a pancreatic trypsin inhibitor homologue and a model inhibitor.
The Journal of Biological Chemistry, vol. 260, No. 21, Sep. 25, 1986, pp. 11451-11455, E. Fioretti et al., Primary structure and antiproteolytic activity of a Kunitz-type inhibitor from Bovine spleen.
EMBO Journal, vol. 5, No. 12, 1986, pp. 3219-3225, B. von Wilcken-Bergmann et al., A synthetic operon containing 14 bovine pancreatic trypsin inhibitor genes is expressed in E. coli.
ADV. Exp. Med. Biol., 1983, pp. 329-337; H. Tschesche et al., Peptide/protein inhibitors of trypsin and kallikrein-primary structural requirements.
Journal of Biological Chemistry, vol. 261, No. 15, Jun. 5, 1986, pp. 7115-7118, C. Berman Marks et al., Production of native, correctly folded bovine pancreatic trypsin inhibitor by *Escherichia coli*.

Primary Examiner—Robert A. Wax
Assistant Examiner—Keith C. Furman
Attorney, Agent, or Firm—Sprung Horn Kramer & Woods

[57] ABSTRACT

Peptides having essentially the sequence of bovine pancreatic trypsin inhibitor (aprotinin) wherein one or more of the amino acids at positions 15, 16, 17, 18, 34, 39 and 52 are replaced by any naturally occurring amino acid produced by recombinant DNA technology, process, expression vector and recominant host therefor and pharmaceutical use thereof. Such peptides being useful as therapeutic agents in diseases connected with the presence of excessive amounts of proteinases.

10 Claims, 24 Drawing Sheets

FIG.2

| | | |
|---|---|---|
| Fra | 1 | AATTCATGCGTCCGGACTTCTGCCTCGAGC |
| Fra | 2 | CAGAAGTCCGGACGCATG |
| Fra | 3 | CGCCGTACACTGGGCCCTGCGTTGCT |
| Fra | 4 | CCCAGTGTACGGCGGCTCGAGG |
| Fra | 5 | CGTATCATCCGTTACTTC |
| Fra | 6 | ATGATACGAGCAACGCAGGG |
| Fra | 7 | TACAATGCAAAGGCAGGCCTGTGTCAGACC |
| Fra | 8 | CCTGCCTTTGCATTGTAGAAGTAACGG |
| Fra | 9 | TTCGTATACGGCGGTTGCCGTGCTAAGCGT |
| Fra | 10 | AACCGCCGTATACGAAGGTCTGACACAGG |
| Fra | 11 | AACAACTTCAAATCCGCGGAAGACTGCGAA |
| Fra | 12 | ATTTGAAGTTGTTACGCTTAGCACGGC |
| Fra | 13 | CGTACTTGCGGTGGTGCTTAGTAAAGCTTG |
| Fra | 14 | CACCGCAAGTACGTTCGCAGTCTTCCGCGG |
| Fra | 16 | GATCCAAGCTTTACTAAGCAC |

FIG.3

```
              Xho
               I
               ↓                                              Apa
                                                               I
                                                               ↓
      ArgProAspPheCysLeuGluProProTyrThrGlyProCys            –
    AATTCATGCGTCCGGACTTCTGCCTCGAGCCGCCGTACACTGGGCCCTGC         50
    ----+----+----+----+----+----+----+----+----+----+     –
        GTACGCAGGCCTGAAGACGGAGCTCGGCGGCATGTGACCCGGGACG
                                                S
                                                t
                                                u
                                                I
      ValAlaArgIleIleArgTyrPheTyrAsnAlaLysAlaGlyLeuCysGln    –
 51 GTTGCTCGTATCATCCGTTACTTCTACAATGCAAAGGCAGGCCTGTGTCA       100
    ----+----+----+----+----+----+----+----+----+----+     –
    CAACGAGCATAGTAGGCAATGAAGATGTTACGTTTCCGTCCGGACACAGT

ThrPheValTyrGlyGlyCysArgAlaLysArgAsnAsnPheLysSerAla   –
101 GACCTTCGTATACGGGGGTTGCCGTGCTAAGCGTAACAACTTCAAATCCG       150
    ----+----+----+----+----+----+----+----+----+----+     –
    CTGGAAGCATATGCCCCAACGGCACGATTCGCATTGTTGAAGTTTAGGC
                                                H
                                                i
                                                n
                                                d
                                                III
      GluAspCysGluArgThrCysGlyGlyGlyAlaEnd
    S CGGAAGACTGCGAACTACTTGCGGTGGTGCTTAGTAAGCTTG
    s
    t
 151 ----+----+----+----+----+----+----+----+----+----+
    2 GCCTTCTGACGCTTGCATGAACGCCACCACGAATCATTTCGAACCTAG
```

FIG. 5A

```
                                                     ApaI
          ArgProAspPheCysLeuGluProProTyrThrGlyProCys
     XhoI
  1  AATTCATGCGTCCGGACTTCTGCCTCGAGCCGCCGTACACTGGGCCCTGC
     ----+----+----+----+----+----+----+----+----+----+  50
     GTACGCAGGCCTGAAGACGGAGCTCGGCGGCATGTGACCCGGGACG

ValAlaArgIleIleArgTyrPheTyrAsnAlaLysAlaGlyLeuCysGln
                                              StuI
 51  GTTGCTCGTATCATCCGTTACTTCTACAATGCAAAGGCAGGCCTGTGTCA
     ----+----+----+----+----+----+----+----+----+----+  100
     CAACGAGCATAGTAGGCAATGAAGATGTTACGTTTCCGTCCGGACACAGT

ThrPheValTyrGlyGlyCysArgAlaLysArgAsnAsnPheLysSerAla
                                                 HindIII
101  GACCTTCGTATACGGGCGGTTGCCGTGCTAAGCGTAACAACTTCAAATCCG
     ----+----+----+----+----+----+----+----+----+----+  150
     CTGGAAGCATATGCCGCCAACGGCACGATTCGCATTGTTGAAGTTTAGGC
     SspI GluAspCysGluArgThrCysGlyGlyGlyAlaEnd
151  CGGAAGACTGCGAACGTACTTGCGGTGGTGCTTAGTAAAGCTTG
     ----+----+----+----+----+----+----+----+----  
     GCCTTCTGACGCTTGCATGAACGCCACCACGAATCATTTCGAACCTAG
```

FIG.6A

```
                                                    XhoI                              ApaI
         ArgProAspPheCysLeuGluProProTyrThrGlyProCys —
      AATTCATGCGTCCGGACTTCTGCCTCGAGCCGCCGTACACTGGGCCCTGC
  1   ———————+—————————+—————————+—————————+—————————+    50
      GTACGCAGGCCTGAAGACGGAGCTCGGCGGCATGTGACCCGGGACG

Stu I
         ValAlaArgIleIleArgTyrPheTyrAsnAlaLysAlaGlyLeuCysGln —
      GTTGCTCGTATCATCCGTTACTTCTACAATGCAAAGGCAGGCCTGTGTCA
 51   ———————+—————————+—————————+—————————+—————————+   100
      CAACGAGCATAGTAGGCAATGAAGATGTTACGTTTCCGTCCGGACACAGT

ThrPheValTyrGlyGlyCysArgAlaLysArgAsnAsnPheLysSerAla —
      GACCTTCGTATACGGGGGTTGCCGTGCTAAGCGTAACAACTTCAAATCCG
101   ———————+—————————+—————————+—————————+—————————+   150
      CTGGAAGCATATGCCGCCAACGGCACGATTCGCATTGTTGAAGTTTAGGC
                                                    HindIII
      Ssl2
         GluAspCysGluArgThrCysGlyGlyGlyAlaEnd
      CGGAAGACTGCGAACGTACTTGCGGTGGTGCTTAGTAAAGCTTG
151   ———————+—————————+—————————+—————————+
      GCCTTCTGACGCTTGCATGAACGCCACCACGAATCATTTCGAACCTAG
```

FIG. 7

```
  Cys Val Ala Leu Ile Ile Arg Tyr Phe Tyr Asn Ala Lys Ala
  CTGCGTTGCTCTCATCATCCGTTACTTCTACAATGCAAAGGCAGG
  ----+---------+---------+---------+---------+
  CCGGGACGAGAAGTAGTAGGCAATGAAGATGTTACGTTTCCGTCC

Leu Cys Gln Thr Phe Val Try Gly Gly Cys Glu Ala Lys Arg Asn Asn Phe Lys Ser
  CCTGTGTCAGACCTTCGTATACGGGGTTGCGAAGCTAAGCGTAACAACTTCAAATCCGC
  ----+---------+---------+---------+---------+---------+
  GGACACAGTCTGGAAGCATATGCCGCCAACGCTTCGATTCGCATTGTTGAAGTTTAGG

Glu Asp Cys Met Arg Thr Cys Gly Gly Gly Ala End
  GGAAGACTGCATGCGTACTTGCGGTGGTGGTGCTTAGTAAAGCTTG
  ----+---------+---------+---------+---------+
  CGCCTTCTGACGTACGCATGAACGCCACCACCACGAATCATTTCGAACCTAG

Glu Asp Cys Thr Arg Thr Cys Gly Gly Gly Ala End
  GGAAGACTGCACCCGTACTTGCGGGTGGTGCTTAGTAAAGCTTG
  ----+---------+---------+---------+---------+
  CGCCTTCTGACGTGGGCATGAACGCCACCACGAATCATTTCGAACCTAG
```

FIG. 11A

EcoRI
→

```
         -100      -90       -80       -70       -60       -50
          •         •         •         •         •         •
GAATTCTCCAGTCTTCACAACAATTGAAAGGAGGAAGCTGAAGAAAGAGTAAGAGGAATT
```

```
         -40       -30       -20       -10        1         10
          •         •         •         •         •         •
TTTGACTCCGCAGTCAGTCTTCAAAAATCAAATAAGGAGTGTCAAAA ATG TTT AAA AAA
                                         SD     Met Phe Lys Lys
```

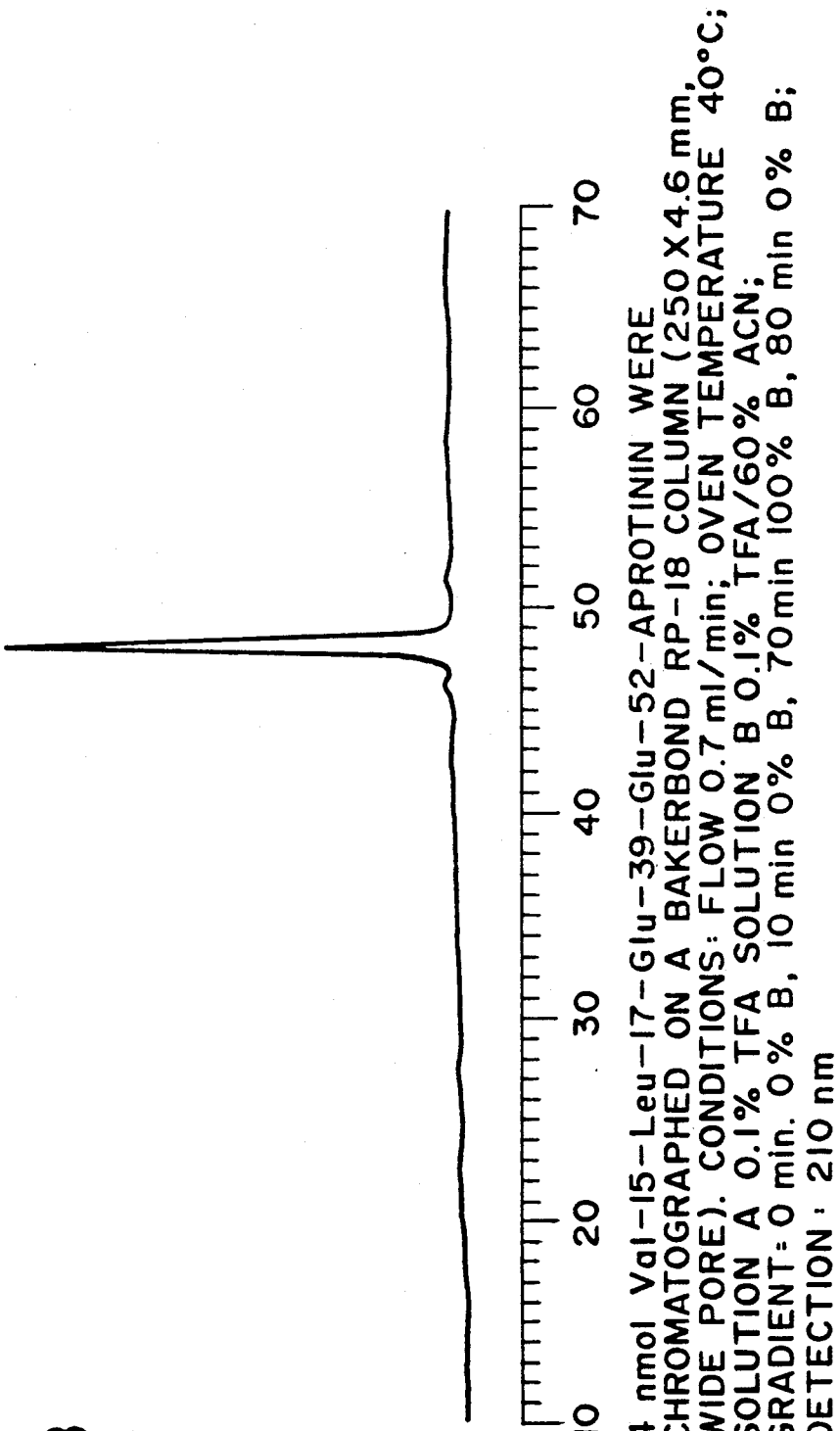

VARIANTS OF BOVINE PANCREATIC TRYPSIN INHIBITOR AND PHARMACEUTICAL USE THEREOF

BACKGROUND OF THE INVENTION

Aprotinin is a well characterized basic protein of 58 amino acids which acts as inhibitor of such proteinases as trypsin, chymotrypsin, plasmin and kallikrein. It has become a valuable drug, named Trasylol ®, for the treatment of various diseases such as, e.g., hyperfibrinolytic hemmorrhage and traumatic hemmorrhagic shock.

Recently it has been demonstrated that the replacement of the residue lysine in position 15 of the aprotinin molecule by other amino acids results in valuable proteinase inhibitors with a modified spectrum of inhibition compared to aprotinin (H. Tschesche et al. (1985), patent application DOS 33 39 693 of May 15, 1985. Depending on the amino acid introduced these modified inhibitors may, e.g., act as inhibitors of the elastases from pancreas and from leukocytes and/or plasma kallikrein. Although aprotinin variants may be obtained by semisynthetic conversion of aprotinin (H. Tschesche et al., DE-OS 33 39 693). The amounts obtainable are relatively small. In addition the methodology does not allow multiple replacements of amino acids in addition to the lysine residue in position 15.

It was, therefore, perceived that the application of recombinant DNA and associated technologies would be the most appropriate way of producing large quantities of aprotinin homologues with the desired specifity and efficacy of inhibition.

To those skilled in the art DNA coding for proteins of known amino acid sequence may be prepared using the genomic DNA-sequence or the cDNA-sequence which is complementary to the mRNA. Amino acid replacements may then be introduced by, e.g., site-directed mutagenesis. Another possibility of obtaining DNA coding for a protein of known primary structure is to choose codons according to the genetic code and to prepare a synthetic gene.

Methods for the expression of heterologous DNA in a recombinant microorganism and/or in eucaryotic cells are known.

SUMMARY OF THE INVENTION

It is an object of the present invention to provide pharmaceutically useful polypeptides/proteins having a high degree of specificity combined with a high inhibitory potency. Said polypeptides are peptides with the amino acid sequence of aprotinin and variants thereof which can be produced by recombinant DNA technologies. The term "variants" refers to polypeptides in which one or more of the amino acids in the original aprotinin sequence are replaced by other naturally occuring amino acids. Preferred positions for such replacements are positions which are in close contact with the target enzyme within the enzyme-inhibitor complex. These are the positions 12, 13, 14, 15, 16, 17, 18, 34, 36, 37, 38 and 39. Not included in the contact region is position 20, but its basic nature may be important in some cases for kallikrein inhibition.

Accordingly the present invention is related to peptides having essentially the sequence of bovine pancreatic trypsin inhibitor (aprotinin, BPTI) wherein one or more of the amino acids at positions 15, 16, 17, 18, 34, 39, and 52 are replaced by any naturally occuring amino acid except 1. aprotinin having a replacement in the 15 position by any of the amino acids Gly, Ala, Val, Leu, Ile, Met, Arg, Thr, Phe, Ser, Trp or Tyr.
2. aprotinin having in addition to a replacement in position 15 as described under 1. an additional replacement in position 52 by any of the amino acids Glu, Leu, Val, Thr or Ser.
3. aprotinin variants as described unter 1. and 2. with an additional Met preceeding the N-terminal amino acid Arg-1, and
4. Val-15-Ser-16-Ile-17-aprotinin.

Preferred are accordingly also peptides which comprise in position 15 the amino acid Leu, Ile, Val, Phe, Tyr, Trp, Met, Ala, Thr, Ser, Gln, Asn, Arg or Lys position 16 the amino acid Val, Met, Thr, Ser, Gln, Asn, Gly, Arg or Ala position 17 the amino acid Leu, Ile, Val, Phe, Tyr, Trp, Met, Ala, Thr, Ser, Gln, Asn, Gly, His, Lys or Arg position 18 the amino acid Leu, Ile, Val, Phe, Met, Thr, Glu or Gly position 34 the amino acid Leu, Ile, Val, Phe, Tyr, Trp, Ala or Thr position 39 the amino acid Leu, Ile, Val, Phe, Tyr, Trp, Met, Ala, Thr, Ser, Glu, Gln, Asn, Gly, Arg, Lys, Asp or Pro and in position 52 the amino acid Leu, Ile, Val, Met, Thr, Ser, Glu, Gln, Asp, Lys or Arg.

More preferably the invention is related to 1. peptides which comprise in
   position 15 the amino acid Val, Leu or Ile,
   position 17 the amino acid Leu, Ile, Val, Gln, Thr, Met, Trp, Tyr, Phe, Asn or Arg,
   position 39 the amino acid Glu, Asp, Asn, Thr, Val, Leu, Ile, Gln or Arg and in
   position 52 the amino acid Thr, Glu or Met.
2. peptides which comprise in
   position 15 the amino acid Val, Leu or Ile
   position 17 the amino acid Leu, Ile, Val, Gln, Thr, Met, Trp, Tyr, Phe, Asn or Arg,
   position 39 the amino acid Glu or Arg and in
   position 52 the amino acid Thr, Glu or Met.
3. peptides which comprise in
   position 15 the amino acid Val, Leu or Ile,
   position 17 the amino acid Leu, Ile, Val or Arg,
   position 39 the amino acid Glu or Arg and in
   position 52 the amino acids Thr, Glu or Met and
4. peptides which comprise in
   position 15 the amino acid Val or Leu
   position 17 the amino acid Leu
   position 39 the amino acid Glu or Arg and in
   position 52 the amino acid Thr, Glu or Met.

Most preferably the invention is related to peptides being

Val-15-Leu-17-
Val-15-Leu-17-Glu-52-
Val-15-Leu-17-Thr-52-
Val-15-Leu-17-Glu-39-
Val-15-Leu-17-Glu-39-Glu-52-
Val-15-Leu-17-Glu-39-Thr-52-
Leu-15-Leu-17-
Leu-15-Leu-17-Glu-52-
Leu-15-Leu-17-Thr-52-
Leu-15-Leu-17-Glu-39-
Leu-15-Leu-17-Glu-39-Glu-52-
Leu-15-Leu-17-Glu-39-Thr-52-aprotinin.

The invention also relates to positions within the molecule which are important for certain ways of expression of the proteins via recombinant DNA technology, specifically position 52.

The invention further relates to polypeptides/ proteins having the sequences as outlined above which in addition contain methionine in position −1 and/or a leader peptide. The term "leader peptide" refers in the context of this application not only to signal sequences promoting secretion of the expression product but also to sequences containing a signal sequence and a linker sequence preceeding the aprotinin or the aprotinin variant sequences. In addition the term "leader sequence" refers to sequences at both ends of the molecule which allow high expression and/or serve to facilitate the purification of the molecules.

The present invention relates also to polypeptides/-proteins having the sequences as outlined above, however, which are shortened by one or several amino acids at one or both ends of the molecule such that inhibitory activity is partly or fully retained.

Homologues (variants) of aprotinin as specified above can be used therapeutically in diseases connected with the presence of excessive amounts of proteinases, e.g., pancreatic elastase (pancreatitis), serum elastase (arteriosclerosis), leukocyte elastase in chronic and acute inflammation with damage of connective tissue, in damage to vessel walls, in necrotic diseases and degeneration of lung tissue. Equally important is the role played by lysosomal enzymes, in particular leukocyte elastase, in inflammatory reactions due to immunological processes, e.g., rheumatoid arthritis, or as myocardial depressant factor and in shock syndromes.

It was perceived that the application of recombinant DNA and associate technologies would be the most appropriate way of producing large quantities of aprotinin homologues with the desired specifity and efficacy of inhibition.

It has also been demonstrated that homologues of aprotinin can be obtained by recombinant DNA technology using a construction in which synthetic genes are fused to the lac Z gene (E. Auerswald et al. (1985), UK patent application 8607523 or unfused (Wilken-Bergmann et al. (1986), *EMBO J.*, 5, 3219-3225). In addition the natural coding region of aprotinin has been expressed as a fusion with the signal sequence of the pho A gene (alkaline phosphatase) (B. Marks et al. (1986), *J. Biol. Chem.*, 204, 7115-7118).

It is often easier to achieve high expression of particularly small heterologous proteins in a bacterial host using gene fusions. This is due to a variety of reasons. Factors seemingly influencing the accumulation of heterologous polypeptides in a host cell include the following:

(1) The heterologous polypeptide may be efficiently degraded by host cell proteinases.
(2) The heterologous polypeptide may have toxic effects upon the cell.

Although a wide variety of heterologous proteins with molecular weights greater than 10,000 daltons have been successfully expressed intracellularly in *E. coli*, relatively few small heterologous polypeptides have been expressed successfully, despite numerous attempts to do so.

A number of efforts to overcome the problem have used fusion polypeptides. The disadvantages of such an approach include among others:

(1) The inserted structural sequence must be in the proper reading frame relative to the AUG start codon of the fusion partner.
(2) The heterologous polypeptide must be cleaved out from the fusion polypeptide chemically or enzymatically. Therefore, the desired protein must be free of the respective cleavage sites. This fact presents in many cases a serious problem.

However, it is sometimes possible to express small polypeptides using plasmids containing multiple copies of the gene (Wilcken-Bergmann et al. (1986), *EMBO J.*, 5, 3219-3225).

Another possibility to overcome the problem of degradation and/or toxicity is to express the heterologous protein in a secretion system. Bacterial, yeast or fungal secretion systems may be used. To obtain secretion an appropriate leader sequence has to be attached to the 5′-end of the gene of aprotinin or aprotinin variants in such a way that the corresponding amino acid sequence in front of the N-terminus comprises a processing site for the signal peptidase which processes the protein to be secreted.

The present invention relates to the synthetic DNA's coding for aprotinin homologues. In particular it is related to a DNA, hereinbelow called "master gene", which has the sequence shown in FIG. 3 and/or functional equivalents thereof. The term "functional equivalents" means in the context of this application that also derivatives of the above DNA sequence in which in some codons one, two or three of the bases are replaced by another base without having an effect on the amino acid to be incorporated into the protein (degeneracy of the genetic code).

In order to produce variants of the aprotinin molecule the master gene is modified by means of recombinant DNA technologies (e.g., site-directed mutagenesis) in such a way that the codon for a certain amino acid is replaced by the codon for another amino acid. Using this approach the various DNA-sequences coding for the aprotinin homologues (for the above mentioned aprotinin variants) according to the present invention can be obtained.

Codons in such replacements are the codons for the preferred amino acids as listed on pages 2, 3, 4, and 5. Depending on the expression system used, the DNA of the present invention can also be a DNA coding for one of the polypeptides variants listed in table 1 carrying upstream of the 5′-end additional sequences.

A further object of the present invention are expression vectors (plasmids) containing the DNA coding for the polypeptides. These plasmids are used for the transformation of a host organism. The present invention also relates to such transformed organisms. A large number of various organisms are known to those skilled in the art as being suitable for transformation. The nature of the plasmid is mainly dependent on the host organism to be used.

The host organism transformed with the plasmid containing the DNA's of the present invention is used for the production of aprotinin homologues. The production comprises the following steps:

(1) cultivating the host organism under appropriate conditions,
(2) recovering the peptides from the culture and
(3) purifying the peptides.

Purification of the polypeptides can be achieved by known methods of protein chemistry such as, e.g., precipitation, chromatography and electrophoresis. The above mentioned linker peptides can be a good tool in such purification since its characteristics can be used to facilitate purification (an example is given by S. J. Bruyer and H. M. Sassenfeld (1985), *Trends in Biotechnology*, 3, 119–122).

The present invention also relates to pharmaceutical compositions and preparations comprising the peptides as outlined above and the use of said peptides in the preparation of pharmaceutical compositions. Such pharmaceutical compositions are very useful in the indications described above.

bRIEF DESCRIPTION OF THE DRAWINGS

FIG. 2 depicts DNA sequences of 15 oligonucleotide fragments used for construction of a synthetic Val-15-Glu-52 aprotinin gene.

FIG. 3 depicts a DNA sequence of a synthetic Val-15-Glu-52-aprotinin master gene in plasmid pRK 54.1.1.

FIG. 5A is a DNA sequence of a Val-15-Leu-17-Glu-52-aprotinin gene.

FIG. 6A is a DNA sequence of a Val-15-Leu-17-Glu-39-Glu-52-aprotinin gene.

FIG. 7 is a DNA sequence of fragments beta-EA10A and B (FIG. 7A), gamma-EA2A and B (FIG. 7B), delta-EA1A and B (FIG. 7C), and delta-EA7A and B (FIG. 7D).

FIG. 17B is a plot depicting the results for HPLC-chromatography of Val-15-Leu-17-Glu-39-Glu-52-aprotinin.

DETAILED DESCRIPTION OF THE INVENTION

Figure 1:
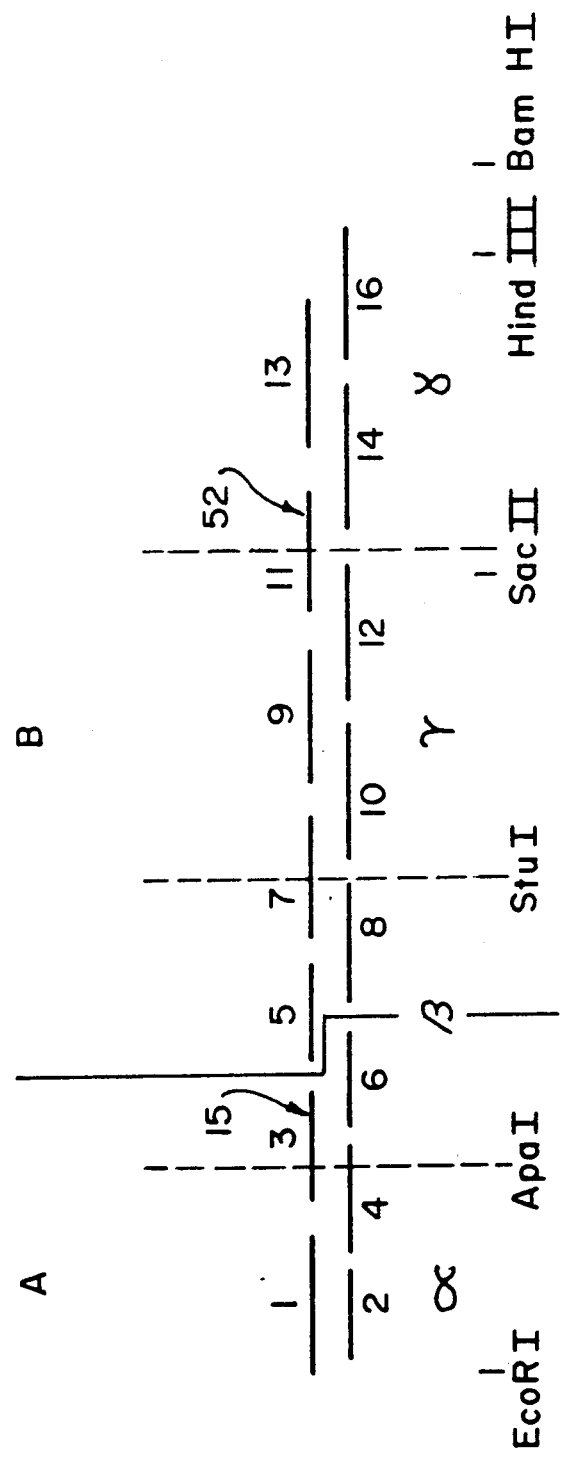
FIG. 1 is a schematic diagram of the design of a synthetic Val-15-Glu-52-aprotinin master gene.

The pharmaceutical preparations which in addition to non-toxic, inert pharmaceutically suitable excipients contain one or more compounds according to the invention, and processes for the production of these preparations.

The present invention also includes pharmaceutical preparations in dosage units. This means that the preparations are in the form of individual parts, for example, tablets, coated tablets, capsules, pills, suppositories and ampoules, of which the content of active compound corresponds to a fraction or a multiple of an individual dose. The dosage units can contain, for example, one, two, three or four individual doses or one half, one third or one quarter or an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example, starches, lactose, sucrose, glucose, mannitol and silica, (b) binders, for example carboxymethylcellulose, alginates, gelatin and polyvinylpyrrolidone, (c) humectants, for example glycerol, (d) disintegrants, for example, agar-agar, calcium carbonte and sodium carbonate, (e) solution retarders, paraffin and (f) adsorption accelerators, for example, quaternary ammonium compounds, (g) wetting agents, for example, cetyl alcohol and glycerol monostearate, (h) adsorbents, for example, kaolin and bentonite and (i) lubricants, for example, talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be such composition that they release the active compound or compounds only, for preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water soluble or water-insoluble excipients, for example polyethylene glycols, fats, for example cacao fat and higher esters (for example $C_{14}$ alcohol with $C_{16}$ fatty acid) or mixtures of these substances.

Ointments, pastes, creams and gels can contain the customary excipients in addition to the active compound or compounds, for example, animal and vegetable fats, waxes, paraffins, starch, tragacanth, cellulose derivatives, polyethylene glycols, silicones, bentonites, silica, talc and zinc oxide, or mixtures of these substances.

Powders and sprays can contain the customary excipients in addition to the active compound or compounds, for example, lactose, talc, silica, aluminium hydroxide, calcium silicate and polyamide powders, or mixtures of these substances. Sprays can additionally contain the customary propellants, for example, chlorofluorohydrocarbons.

Solutions and emulsions can contain the customary excipients in addition to the active compound or compounds, such as solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cotton seed oil, groundnut oil, corn germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solution and emulsions can also be in a sterile form which is isotonic with blood.

Suspensions can contain the customary excipients in addition to the active compound or compounds, such as liquid diluents, for example, water, ethyl alcohol or propylene glycol, suspending agents, for example, ethoxylated isostearyl alcohols, polyoxyethylene sorbitol and sorbitan esters, microcrystalline cellulose, aluminium metahydroxide, bentonite, agar-agar and tragacanth, or mixtures of these substances.

The formulation forms mentioned can also contain dyestuffs, preservatives and additives which improve the odor and flavor, for example, peppermint oil and eucalyptus oil, and sweeteners, for example, saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example, by mixing the active compound or compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 0.5 to about 500, preferably 5 to 100, mg/kg of body weight every 24 hours, optionally in the form of several individual administrations, in order to achieve the desired results. An individual administration contains the active compound or compounds according to the invention preferably in amounts of about 1 to about 250, in particular 3 to 60, mg/kg of body weight. However, it can be necessary to deviate from the dosages mentioned and, in particular, to do so as a function of the nature and body weight of the subject to be treated, the nature and severity of the illness, the nature of the preparation and of the administration of the medicine, and the time or interval over which the administration takes place.

Thus, it can suffice in some cases to manage with less than the abovementioned amount of active compound, whilst in other cases the abovementioned amount of active compound must be exceeded. The particular required optimum dosage and the type of administration of the active compounds can easily be decided by anyone skilled in the art on the basis of his expert knowledge.

SYNTHETIC GENES

In the following, the strategy for the synthesis of genes coding for aprotinin and aprotinin homologues is described:

The known protein sequence of aprotinin and its homologues and the genetic code were used to design a DNA sequence coding for these polypeptides. All possible base substitutions (degeneracy of the genetic code) as well as all potential restriction sites were also considered in the design of the synthetic DNA sequence.

The resulting principal design for a synthetic aprotinin gene and the homologues is shown in FIGS. 1, 2, and 3. The synthetic master gene consists of four blocks (named $\alpha$, $\beta$, $\gamma$, $\delta$) each of which carries recognition sites for restriction endonucleases at both ends (see also Example 3, FIG. 1). This allows easy modification and alteration of the DNA sequences (codon usage, mutations, amplification of genes, protein engineering) for, e.g., unfused expression or expression as fusion proteins. Fusion proteins are designed in such a way that the desired protein may be liberated from the fusion by enzymatic or chemical methods or is liberated during the secretion into the periplasmic space.

The total spectrum of protein engineering becomes possible with this construction. Amplification of the gene may be obtained by adding appropriate linker sequences. Amino acid replacements are possible in all positions except those belonging to a recognition site for a restriction endonuclease. These (and all others) may be changed by any one skilled in the art using e.g. site-directed mutagenesis. The plasmid chosen for cloning of the synthetic genes was pUC 8 (J. Vieira and J. Messing (1982), *Gene*, 19, 259). The plasmid is commercially available from P-L Biochemicals. The synthetic genes were cloned in pUC 8 and sequenced directly by the supercoil DNA sequencing method (K. J. Chen and P. H. Seaburg (1985), *DNA*, 4, 165-170).

EXPRESSION PLASMIDS

For expression of aprotinin homologues as fusion proteins plasmids were used in which the appropriate gene was fused to (1) the 3'-end of the coding region of the lac Z gene ($\beta$-galactosidase) (U. Rüther and B. Müller-Hill (1983), *EMBO J.*, 2, 1791-1794), or (2) the codon of amino acid 98 of the polymerase of phage MS-2 (E. Remault et al. (1981), *Gene*, 15, 81-93).

For expression of aprotinin homologues secreted into the periplasmic space or into the medium the respective gene was cloned into an $\alpha$-amylase secretion vector (M. A. Sullivan et al. (1984), *Gene*, 29, 21-26). The gene was modified by introducing an XbaI-cleavage site at the 5'-end of block $\alpha$. Such a construction allows cleavage of the primary translation product during secretion by the endogenous leader peptidase to yield the desired aprotinin or aprotinin variant.

Insertion of the synthetic aprotinin and aprotinin variant genes in the proper cloning sites and in the correct reading frame leads in all cases to the desired fusion proteins.

*E. coli* strain RRI ΔM15 was transformed with either one of the following three expression plasmids pES 44.1.1, pES 45.1.3 or pCH 2742 and deposited Jun. 26, 1987 at the Deutsche Sammlung von Mikroorganismen, D-3400 Göttingen, Grisebachstr. 8/FRG, under the number indicated:

| E. coli RRI ΔM15 | pES 44.1.1 | DSM 4157 |
| E. coli RRI ΔM15 | pES 45.1.3 | DSM 4158 |
| E. coli RRI ΔM15 | pCH 2742 | DSM 4159 |

EFFICACY OF APROTININ VARIANTS

By changing the amino acid sequence of aprotinin in the positions indicated in Table 1 it was found to our surprise that not only the inhibitory activity towards human leukocyte elastase could be significantly increased but also variants could be found which were potent inhibitors of other serine proteases like human cathepsin G or human pancreatic elastase I.

Examples of aprotinin variants which show increased inhibitory activity against human leukocyte elastase are those which contain the amino acid leucine in position 17. They were found to exhibit a $K_i$-value being better by almost one order of magnitude than found with variants having the original amino acid arginine in position 17. The improvement in efficacy shown by these inhibitors was also demonstrated in more relevant test models, e.g., in a degradation assay using subendothelial matrix or in a model of acute pulmonary inflammation in hamsters.

Examples of aprotinin variants which inhibit in addition to human leukocyte elastase other important leukocyte proteases like cathepsin G are variants which contain the amino acid leucine in positions 15 and 17.

Examples of aprotinin variants which inhibit human pancreatic elastase I are those which contain the amino acid glutamate in position 39 and leucine in position 17.

MATERIALS AND METHODS

The synthetic genes, recombinant plasmids and expression vectors containing the synthetic genes can be prepared and characterized using the following materials and methods:

MATERIALS

1) Enzymes

DNA polymerase, Klenow; T4-DNA ligase (0.9 units/μl); lysozyme; RNase A Polynucleotide Kinase from Boehringer, Mannheim.

Restriction enzymes from Boehringer Mannheim, Bethesda Research Labs and Biolabs were used according to the manufacturers instructions.

2) Reagents

ATP, dATP, TTP from Sigma;

DTE, Thymidine from Serva, Heidelberg;

Saccharose from Bethesda Research Labs;

Diaminopimeleic acid, rubidium chloride from Sigma;

All other reagents were of analytical grade (Merck, Darmstadt and/or Sigma).

3) DNA/Plasmids

Plasmid pUC 8; 5'-phosphorylated Bam H1 linker from P-L Biochemicals (Pharmacia);

Plasmid pUR 278 (U. Rüther and B. Müller-Hill (1983), *EMBO J.*, 2, 1791-1794);

Plasmid pPLc24 was obtained from W. Fiers, University of Gent, Belgium (construction of pPLc24: Remault et al., *Gene*, 15, 81-93 (1981)).

4) Strains

*E.coli* RRI ΔM15 from ATCC (No. 35 102) *E.coli* C 600[pcI 857] was obtained from W. Fiers, University of Gent, Belgium (construction of pcI 857: Remault et al., *Gene*, 22, 103-113 (1983); *E.coli* C600: ATCC 23724).

*Bacillus subtilis* from DSM (No. 704).

5) Media

Bacto-tryptone; Bacto-yeast-extract; Bacto-agar from DIFCO

LB-Medium (for 1 ltr.): 10 g Bacto-tryptone, 5 g Bacto-yeast-extract, 10 g NaCl, adjusted to pH 7.5 with NaOH kappa 1776-Medium (for 1 ltr.): 25 g Bacto-tryptone, 7.5 g Bacto-yeast-extract, 20 ml 1M TRIS-HCl pH 7.5, dissolved in 950 ml distilled water and autoclaved. After cooling was added: 5 ml 1M magnesium chloride, 10 ml 1% diaminopimeleic acid, 10 ml 0.4% thymidine, 25 ml 20% glucose (all added solutions were sterilized by filtration).

Agar plates were prepared by adding 15 g Bacto-agar to 1 ltr. of the appropriate medium.

6) Antibiotics

Chloramphenicol and Kanamycin-sulfate from Boehringer Mannheim.

Ampicillin and Tetracyclin from Serva, Heidelberg.

7) Buffers and solutions 10 mM ATP in water

10X Ligase-mix: 0.5M Tris-HCl (pH 7.4); 0.1M $MgCl_2$; 0.1M DTE; 10 mM ATP

10X SP-50: 100 mM Tris-HCl (pH 7.5); 100 mM $MgCl_2$; 500 mM NaCl; 10 mM DTT

10X SP-100: 100 mM Tris-HCl (pH 7.5); 100 mM $MgCl_2$; 1M $CaCl_2$; 10 mM DTT

10X SP-O: 100 mM Tris-HCl (pH 7.5); 100 mM $MgCl_2$; 10 mM DTT

20X E-buffer: 0.8M Tris; 0.4M sodium acetate; 40 mM EDTA; pH 8.3 $ZnCl_2$, 10 mM Spermidine.

Transformation buffer (prepared as follows): 15 g saccharose, 1 ml 3.5M KOH, 1 ml 1M $CaCl_2$, 2 ml 5.0M RbCl, bring to 50 ml with aqua bidest., adjust to pH 6.2 with 10% acetic acid, add 1 ml 4.5M $MnCl_2$, adjust to pH 5.8 with 10% acetic acid, fill to 100 ml with aqua bidest. and filter sterile.

TE buffer: 10 mM Tris-HCl pH 8.0, 0.1 mM EDTA

2510 X NT-buffer: 0.5M Tris-HCl pH 7.2; 0.17 $MgSO_4$, 1 mM DTE

Lysozyme mix: 50 mM glucose, 2 mg/ml in 1 mM EDTA, 10 mM Tris-HCl pH 8.0 freshly prepared prior to use Phenol/Sevag: mixture of 1 volume 80% phenol and 1 volume Sevag (Chloroform: iso-amylalcohol, 24:1)

TEABC-buffer: 1M Triethylamine in distilled water, pH adjusted to 7.5 with gaseous $CO_2$ 10X PNK-Mix: 0.5 Tris-HCl (pH 7.6), 0.1M $MgCl_2$, 50 mM MDTE, 1 mM EDTA 10X Ligase-Mix: 0.5M Tris-HCl (pH 7.4), 0.1M $MgCl_2$, 0.1M DTE, 10 mM ATP.

METHODS

Standard Methods for recombinant DNA work were used as described in Maniatis et al. (1982), *Molecular*

*Cloning*, Cold Spring Harbor Laboratory, Cold Spring Harbor, USA:

STANDARD ETHANOL PRECIPITATION

DNA pellets were dissolved or solutions were adjusted to 0.3M sodiumacetate, two volumes of ethanol were added, incubated at −70° C. for 15 minutes and centrifuged. Pellets were washed twice with 80% ethanol and dried under vacuum.

STANDARD PHENOL EXTRACTION

Solutions were mixed thoroughly with phenol/sevag (1:1), centrifuged and the phenol phase was reextracted with 1/10 volume of TE-buffer or water. The aqueous phases were pooled.

STANDARD DEPHOSPHORYLATION OF DNA

DNA completely digested and purified was dissolved in water and adjusted to 1X CIP-buffer (standard total volume 48 μl). Reaction was started at 37° C. by addition of 1 μl (20 units) calf intestine phosphatase (CIP) after 30 minutes again 1 μl CIP was added. Reaction was stopped after 1 hour by adding 5 μl of 50 mM EGTA and incubation at 65° C. for 10 minutes. For dephosphorylation of DNA with blunt ends or recessed 5' termini, repeated incubations were done for 15 minutes at 37° C. and for 15 min at 56° C. respectively. The DNA was extract with phenol/sevag and precipitated with ethanol.

STANDARD LIGATION

For standard ligations a 5-fold molar excess of fragment over vector was used. Final DNA concentration was 25 μg/ml. DNA was dissolved in a small amount of TE-buffer. Ligation was performed with T4 DNA ligase in 1 · Ligase mix (50 mM TRIS-HCl pH 7.4, 10 mM MgCl$_2$, 10 mM DTE, 1 mM ATP) in a standard volume of 30 μl for 16 hours at 14° C.

STANDARD RESTRICTION ENDONUCLEASE DIGESTION

Restriction endonuclease digestions were carried out mainly according to the manuals of the suppliers.

Purified salt free DNA was dissolved in buffer (SP-0, SP-50 or SP-100 depending on the enzyme used) and digested with an appropriate amount of enzyme. Finally material was phenol extracted and ethanol precipited.

STANDARD ISOLATION OF DNA FRAGMENTS AFTER AGAROSE GEL ELECTROPHORESIS

DNA fragments were separated by agarose gel electrophoresis (see T. Maniatis et al., 1982, Cold Spring Harbor Laboratory, *Molecular Cloning*) stained with Ethidium bromide and cut out under long wave UV light. Slices were put into a dialysis bag, filled with 0.5X E-buffer (volume ratio, buffer:gel slice as 1.5:1) and must be well surrounded by buffer. The sealed bag, air bubble free, was placed into an electrophoresis chamber filled with 0.5X E-buffer. Electrophoresis was carried out for 30 min at 200 V, than polarity of the current was reversed for 30 seconds to release the DNA from the wall of the dialysis bag. The buffer surrounding the gel slice was carefully removed and purified further on DEAE cellulose or DE 52 columns (see above).

STANDARD TRANSFORMATION PROCEDURE

Transformations were performed using the procedure of D. Hanahan ((1983), *J. Mol. Biol.*, 166, 557–580).

1 ml of a 20 ml overnight culture of the host strain inoculated with a single colony and grown in kappa 1776 medium (37° C., shaker with 200 upm), was used to inoculate 100 ml of prewarmed (37° C.) kappa 1776 medium.

This culture was cultivated under the same conditions. Cell growth was stopped at 0.2 OD (500 nm). After cooling to 4° C. and centrifugation, cell pellet was resuspended in 20 ml ice-cold transformation buffer and incubated at 0° C. for 5 minutes. The suspension was centrifuged again (3000 rpm, 4° C., 15 minutes) and the pellet resuspended in 4 ml ice-cold transformation buffer. After adding 7 μl DMSO to 200 μl aliquots, cells were incubated further in ice water for 15 to 60 minutes. To such an aliquot of complete cells DNA, dissolved in 20 μl TE-buffer, was added and the mixture incubated in ice water for 20 minutes followed by 3 minutes at 42° C. 1 ml of prewarmed (37° C.) kappa 1776 medium was then inoculated with such an aliquot and cultivated at 37° C. for 1 hour. For plating the transformants, cells were spun down (3000 rpm, 15 minutes, 4° C.), resuspended in YT medium an plated on indicator plates. According to the expected number of transformants an appropriate amount of the suspension was used for plating.

STANDARD RAPID ANALYTICAL PLASMID ISOLATION

The procedure described is a modification of the method of H. C. Birnboim and J. Doly (1979), *Nucleic Acids Res.*, 7, 1513); T. Maniatis et al. (1982), Cold Spring Harbour Laboratory, *Molecular Cloning*). From each transformant to be analyzed, a 2 ml overnight culture was prepared (37° C., 16 hours, rotating wheel). 1.5 ml of the culture were centrifuged for 1 minute at 12,000 × g. The pellet was redissolved in a freshly prepared solution of lysozyme mix and incubated at 20° C. for 5 minutes. The sample was further incubated for 5 minutes on ice after addition of freshly prepared ice-cold 0.2M NaOH containing 1% SDS. To precipitate chromosomal DNA and proteins 150 μl ice-cold potassium acetate pH 4.8 was added. After incubation 5 minutes on ice and centrifugation for 10 minutes at 12,000 × g the supernatant was transferred to a fresh tube and extracted with Sevag. 500 μl isopropanol was added to the aqueous phase. The mixture was then incubated for 30 minutes at −20° C. After centrifugation (10 min., 12,000×g) the pellet was washed with 80% ethanol and dried briefly under vacuum.

STANDARD DNA SEQUENCING

Standard DNA sequencing was carried out as described by the manufacturer's protocol (Guidelines for Quick and Simple Plasmid Sequencing, Boehringer Mannheim (1986)).

GROWTH AND INDUCTION OF BACTERIAL STRAINS

Bacterial cultures were propagated in media complemented with appropriate antibiotic(s). To attempt expression of the β-galactosidase-fusion proteins *E. coli* RRI ΔM15 transformed with the expression plasmid pES 44.1.1 or pES 45.1.3 was inoculated into 2 ml LB-ampicillin medium. After 12–16 hours of growth at 37°

C. in shake flasks samples of 1 ml were used directly for inoculation of 100 ml LB-ampicillin medium containing 0.2 mMol IPTG. A clone containing pUR 278 without aprotinin gene insert was cultivated under the conditions to provide for the negative control. After growing for 12-16 hours at 37° C. with agitation, the cells were harvested by centrifugation at 5000 rpm for 10 minutes in 1 Beckman JA 10 rotor.

STANDARD SDS-POLYACRYLAMIDE GEL ELECTROPHORESIS

Detection of proteins was performed with SDS polyacrylamide gel electrophoresis according to Laemmli, U.K. (1970). *Nature*, 277, p. 680, see also B. D. Hames and D. Rickwood 1981, *Gel Electrophoresis of Proteins*, IRL Press Limited, Oxford).

About $1 \cdot 10^9$ cells were centrifuged, redissolved in SDS sample buffer (70 mM Tris, 10% glycerol, 1% SDS, 5% β-mercaptoethanol, 0.1 mM EDTA), incubated for 5 minutes at 95%, and applied to each lane. After electrophoresis gels were stained with Coomassie blue.

AMINO ACID SEQUENCE DETERMINATION

About 0.5-2 nmol of the protein were solubilized in 30 µl TFA. The sample was applied to a glass fibre filter which was pretreated with 3 mg of polybrene. The sequence analysis was performed by the gas phase protein sequencer from Applied Biosystems (Inc. USA) according to Hewick (R. M. Hewick, M. W. Hunkapiller, L. E. Hood, W. Dreger 1981, *J. Biol. Chem.*, 256, 7990-7997). The amino acid phenylthiohydantoin derivatives liberated in each step were analyzed using a cyano-HPLC column (Dupont) and a separation system described by Beyreuther (K. Beyreuther, B. Biesler, J. Bowens, R. Dildrop, K. Neufer, K. Stüber, S. Zais, R. Ehring, P. Zabel (1983), *Modern Methods in Protein Chemistry*, 303-325, Walter de Gruyter—Co., Berlin). A waters HPLC system, including a M 510 pump, a WISP 710B autoinjector, a LC-spectrophotometer M 481, and Shimadzu integrator C-R3A, was used.

ACID HYDROLYSIS AND AMINO ACID ANALYSIS

About 1 nmol of the protein was given in a pyrex tube to which 200 µl 6M HCl constant boiling HCl containing 0.05% 2-mercaptoethanol (I. T. Potts jr. 1969, *Anal. Biochem.*, 131, 1-15) was added. Tubes were sealed under vacuum and incubated at 110° C. for 22 hours. Hydrolysates were quickly dried, redissolved in 150 µl 0.2M sodium citrate buffer pH 2.2 and filtered. Amino acid analysis were carried out with a Biotronic LC 5000 amino acid analyzer equipped with a fluorescence detector and a Shimadzu C-R2AX integrator. Amino acids were quantified after reaction with o-phthaldialdehyde essentially as described by Benson (J. R. Benson, P. E. Hare 1975, *Proc. Natl. Acd. Sci. USA*, 72, 619-622).

INHIBITION ASSAYS FÜR LEUKOZYTE ELASTASE

Leukocyte elastase was determined as described by K. Nakajima et al. (1979): *J. Biol. Chem.*, 254, 4027. The assay conditions were as follows:

| | |
|---|---|
| Substrate (stock solution) | 0.1M Methoxysuccinyl-L-alanyl-L-alanyl-L-prolyl-L-valine-p-nitro-anilide in dimethylformamide. The stock solution was stored at −18° C. |
| Substrate (amount per test) | 6.5 µl |
| Substrate - supplier | Bachem Bubendorf/Schweiz |
| Enzyme (stock solution) | 0.01 mg/ml human leukocyte elastase in 50% ethylene glycol. The solution was stored at −18° C. |
| Enzyme (amount per test) | 5 µl |
| Enzyme - supplier | Elastin Products Company Pacific/USA |
| Buffer | 0.2M Tris/HCl, pH 8.0 − 0.05% Tween 80 |

GENERAL PROCEDURE

The inhibitor sample was diluted with such an amount of buffer, that the final volume (after addition of substrate) was 0.65 ml. Next, the enzyme was added, and the mixture was allowed to stand for 30 minutes at room temperature. Finally, the substrate solution was added, and the increase in optical density at 405 nm was subsequently recorded automatically for each sample. The linear increase of the optical density during the first 10 minutes (ΔOD) was taken as the activity of enzyme.

To determine inhibitory activities the enzymatic activity with and without added inhibitor was measured. Degree of inhibition in % was calculated as follows:

$$\text{inhibition} (\%) = 100 \cdot \left(1 - \frac{\Delta OD_{sample\ with\ inhibitor}}{\Delta OD_{sample\ without\ inhibitor}}\right)$$

DETERMINATION OF THE $K_i$-VALUES FORM THE TITRATION CURVES OF HUMAN LEUKOCYTE ELASTASE WITH THE INHIBITORS

To a series of solutions containing ~200 ng human leukocyte elastase in 900 µl 0.2M Tris-buffer pH 8.0 with 0.05% Tween 80 each, different amounts of the inhibitors are added. The mixtures are kept at room temperature for at least 2 hours after supplementation of the volume to 985 µl with test buffer. Then 15 µl of a mixture composed of 10 µl substrate stock solution—59 mg MeOSuc-Ala-Ala-Pro-Val-pNA per 1 ml dimethylsulfoxide—and 990 µl test buffer are added to each sample after 5 minutes equilibration to 30° C. in a thermostatesized cuvette holder and the increase in optical densities at 405 nm was determined. The $K_i$-values are calculated according to M. W. Empie and M. Laskowski jr., *Biochemistry*, 21, 2274-2284 (1982) using the equation:

$$K_i = \frac{[E_f] \cdot [I_f]}{[EI]}$$

In this equitation $[E_f]$ and $[I_f]$ are the molar concentrations of uncomplexed enzyme and uncomplexed inhibitor respectively; [EI] is the molar concentration of the enzyme inhibitor complex.

EXAMPLES

Example 1

Synthesis and purification of DNA fragments coding for Val-15-aprotinin variants The oligonucleotides which comprise the gene (see FIG. 2) were prepared using solid-phase synthetic methods. The synthetic scheme for the oligomers utilized proton activated, protected 2'-deoxyribonucleotide phosphoramidites. All sequential steps were performed in an automated manner on an Applied Biosystems model 380 DNA synthesizer using protected nucleotides, solvents, chemicals, and reagents obtained from this manufacturer. The solid-phase support, also from the same manufacturer, was controlled pore glass to which the starting 3'-nucleotide was already attached. Certain modifications were introduced into the automated reaction cycle in accordance with the manufacturers operating instructions and users bulletins. Upon completion of the synthesis, the oligomers were deblocked and cleaved from the solid support within the DNA synthesizer according to the manufacturers recommendations.

Removal of the blocking groups was completed by heating the aqueous solution containing the oligomer with concentrated ammonium hydroxide at 55° C. from 4 to 24 hours in a sealed vial. The resulting solution was evaporated, the residue dissolved in 0.01M triethylammonium bicarbonate buffer, pH 7.0 (TEAB buffer). This solution was chromatographed over Sepahdex-G 50 ® gel filtration resin. This column was prepared in and eluted with the same TEAB buffer. Material eluting with the void volume was pooled and the solution evaporated. A portion of the residue (10 to 40% of the absorbance units at 260 nm), dissolved in loading buffer (composition: 0.1% Bromophenol Blue, 0.1% Xylene Cyanol, 10 mm disodium EDTA, in formamide) was further purified by electrophoresis on polyacrylamide gels. The gel size was 18 × 32 cm with a thickness of 1.5 mm. The well size for each oligomer purified in this manner was 2 to 5 cm in width and up to five oligomers were purified using a single gel. The concentration of acrylamide in the gel varied from 14 to 20%, depending on the chain length of the desired product. For longer oligomers, a 14% a acrylamide gel is preferred, while shorter oligomers were purified on up to a 20% acrylamide gel. The gels also contained 7M urea and Tris-borate EDTA buffer (0.1M Tris, 0.1M Borate, 2 mM EDTA ph 8.3). The running buffer was the same Tris-borate EDTA mixture. Electrophoresis was carried out at 20 to 60 watts, constant power, for from 18 to 6 hours. Such standardized techniques are available in various User Information Bulletins available from Applied Biosystems.

Following completion of the electrophoresis, the gel is encased in plastic wrap and the oligomers visualized by shadowing with ultraviolet light. This shadowing is accomplished by placing the wrapped gel on a fluorescent thin layer chromatography plate and viewing the gel with a short wave length ultraviolet light source. The desired product appears as the slowest migrating, major blue DNA fragment by this shadowing techniqued. The desired band is exised from the gel. The DNA oligomer is eluted from the gel slice onto powdered diethylaminoethyl (DEAE) cellulose using an EpiGene D-Gel ® electrophoresis apparatus. The oligomer is recovered from the cellulose by elution with 1M TEAB buffer. The buffer solution containing the oligomer is evaporated, the residue is dissolved in 0.01M TEAB buffer, and then desalted by passage over a column of Sephadex-G 50 ® as described previously. The material eluting in the void volume is pooled and lyophilized to give the final product.

Using the procedures outlined above, about 0.5 to 5.0 A 260 units of each of the purified oligomers was obtained.

Example 2

Construction of a synthetic master gene for Val-15-Glu-52-aprotinin and insertion into plasmid pUC8 to give plasmid pRK 54.1.1

The design of the master gene is shown in FIG. 1. It is composed of the building blocks $\alpha$, $\beta$, $\gamma$, and $\delta$ and constructed by assemblying the 15 purified oligonucleotides shown in FIG. 2. The DNA sequence shown in FIG. 3, includes the initiation codon ATG, two termination codons, TAG and TAA, the terminal restriction sites Eco RI, Hind III and Bam HI and internal restriction sites. The choice of these sites facilitated the cloning of the coding sequence and its modification.

The construction used to generate this synthetic gene employed besides the fragments the use of polynucleotid Kinase, T4 DNA ligase and restriction enzymes as described in detail within material and methods.

Fifteen purified oligonucleotide fragments were dissolved in 50 mM TEABC (Triethylammonium bicarbonate buffer, pH 7.5) final concentration 10 pmol/µl. The phosphorylation of all fragments was done in 4 separate parts (frag. 1,3; frag. 2, 4, 6; frag. 5, 7, 9, 11, 13; frag. 8, 10, 12, 14, 16). For preparative purpose 80 pmol of each fragment, respectively, were dissolved in a mixture of 1X PNK-Mix, 2 µM ATP, 0.5 µCi 32 gamma ATP per 10 pmol fragment, 10 units PNK per pmol fragment, so that the total volumes were for frag. 1, 3: 300 µl; for frag. 2, 4, 6: 400 µl for frag. 5, 7, 9, 11, 13; and frag. 8, 10, 12, 14, 16: 700 µl. Reaction for each part was carried out at 37° C. for 30 min. All parts were phenolized, ethanol precipitated, washed adn dried.

For hybridization purpose frag. 1, 3 and frag. 2, 4, 6 (block A) were dissolved and mixed in 1X ligase-mix, total volume 120 µl, incubated for 5 minutes at 70° C., cooled down to room temperature within 5 hours. The other fragments (block B) were hybridized in 240 µl according to the same procedure.

For ligation purpose, block A solution was supplemented with 12 µl 10 mM ATP, 12 µl 100 mM DTE, 20 µl T4-DNA ligase and block B solution with twice as much. Reaction was carried out at 14° C. for 7 hours. After this 10 µl T4 DNA ligase was added for block A and 20 µl for block B and again incubated at 14° C. for 45 minutes. The mixtures were phenolized, ethanol precipitated and dried.

The obtained block A was dissolved in 90 µl 1X SP-100 and 10 µl Eco RI (10 U/µl), block B in 90 µl 1X SP-50 and 10 µl Bam HI and incubated at 37° C. for 1 hour. The reactions were stopped by phenol extraction and ethanol precipitation, 6% polyacrylamide gel gelectrophoresis was carried out, and the DNA blocks were recovered according to the same procedure as described in Example 1.

Equal amounts of radioactive labelled block A and B were dissolved in water, adjusted to 1X ligase mix and hybridized as described above for final ligation to a synthetic gene. Therefore, 3 µl 10 mM ATP, 3 µl 100 mM DTE. 3 μl T4 DNA ligase were added to 22 μl hybridization mixture and incubated at 14° C. for 7 hours. Again 1 μl T4 DNA ligase was added and this reaction was carried out at 14° C. for 45 minutes. The ligation product was purified by phenol extraction and ethanol precipitation. A standard restriction enzyme digestion (Bam HI 1.5 μl, Eco RI 1.5 μl double digestion) in SP-50 was performed. The material was phenol extracted and before ethanol precipitation the aqueous solution was adjusted to 3 mM MgCl₂ 0.3M sodium acetate. Then 6% polyacrylamine gel electrophoresis was carried out, and the gene was recovered according to the same procedure as described in Example 1.

The synthetic Val-15-Glu-52-aprotinin master gene obtained by this procedure was inserted into a EcoRI/-Bam HI digested pUC8 vector (J. Vieira and J. Messing. *Gene.* 19,259 (1982 as follows:

Purified pUC 8 DNA (about 30 pmol) was digested twice with EcoRI and Bam HI under standard restriction endonuclease digestion conditions, to cut out a small internal EcoRI-Bam HI fragment. This preparation was dephosphorylated with calf intestine phosphatase separated by agarose gel electrophoresis and the large EcoRI-Bam HI fragment of the vector was purified (standard conditions).

Figure 4:
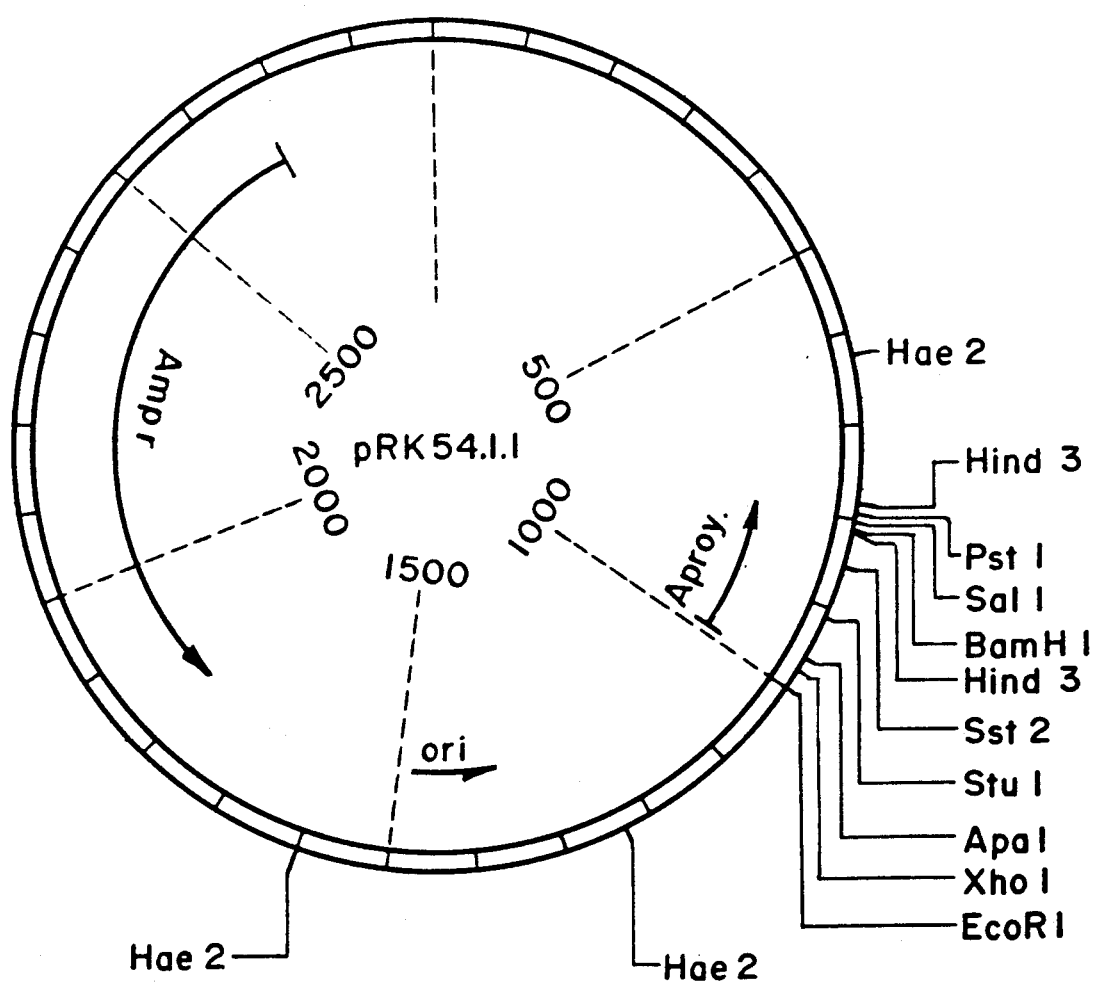
FIG. 4 is a schematic diagram of the restriction map of recombinant plasmid pRK 54.1.1.

The construction of pRK 54.1.1 (see FIG. 4) was done by ligating the total amount of purified synthetic aprotinin gene with 1 pmol vector (1.8 units T4-DNA ligase, 1X ligase mix, total volume 45 μl, incubation at 14° C. for 7 hours, addition of 1 unit T4-DNA-ligase and reincubation at 14° C. for 45 minutes).

Using the transformation procedure from D. Hanahan *E.coli* strain RRI delta M15 (A. Kalnins et al. (1983), *EMBO Journal.* 2, 593; ATCC 35102) was used as host cell. 15 "white" transformants were received on indicator plates containing 200 μg/ml ampicillin. All 15 transformants were screened using a modification of the rapid analytical plasmid isolation method of Birnboim and Doly 1979. Therefore, pellets of the 15 samples were redissolved in 30 μl 1X SP-100 containing 1 μg RNase A. A restriction digestion with Eco RI and Bam HI was performed.

After gel electrophoresis four of the fifteen transformants were found to contain plasmid DNA carrying an Eco RI-Bam HI fragment approximately 200 base pairs long. All transformants which carried this Eco RI-Bam HI fragment were grown in large scale and plasmids from each were isolated and analyzed further. Two of them were sequenced by the standard, sequencing procedure as described in Material and method's all showed the sequence of the Val-15-Glu-52-aprotinin gene.

EXAMPLE 3

Figure 5B:
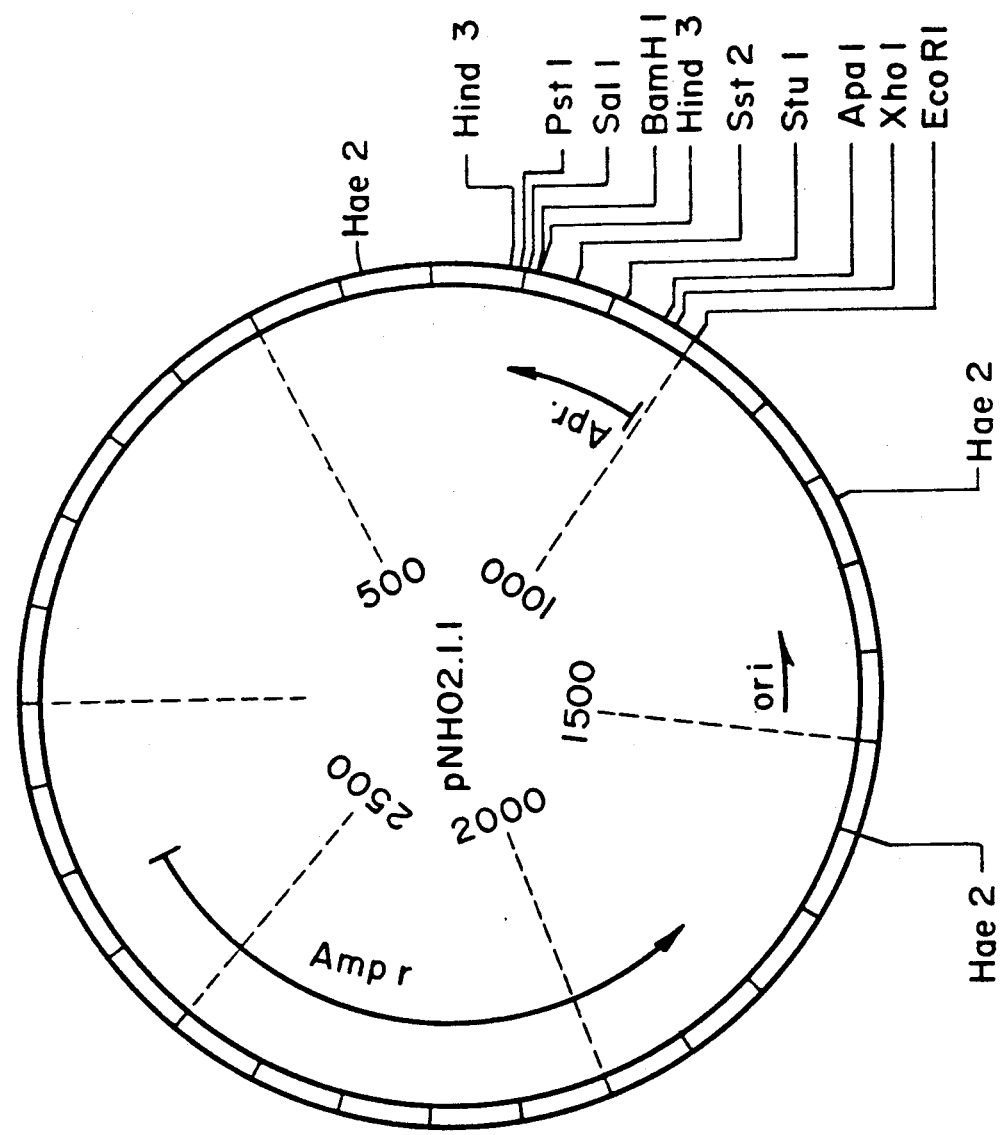
FIG. 5B is a schematic diagram of the restriction map of recombinant plasmid pNH 02.1.1.
Figure 6B:
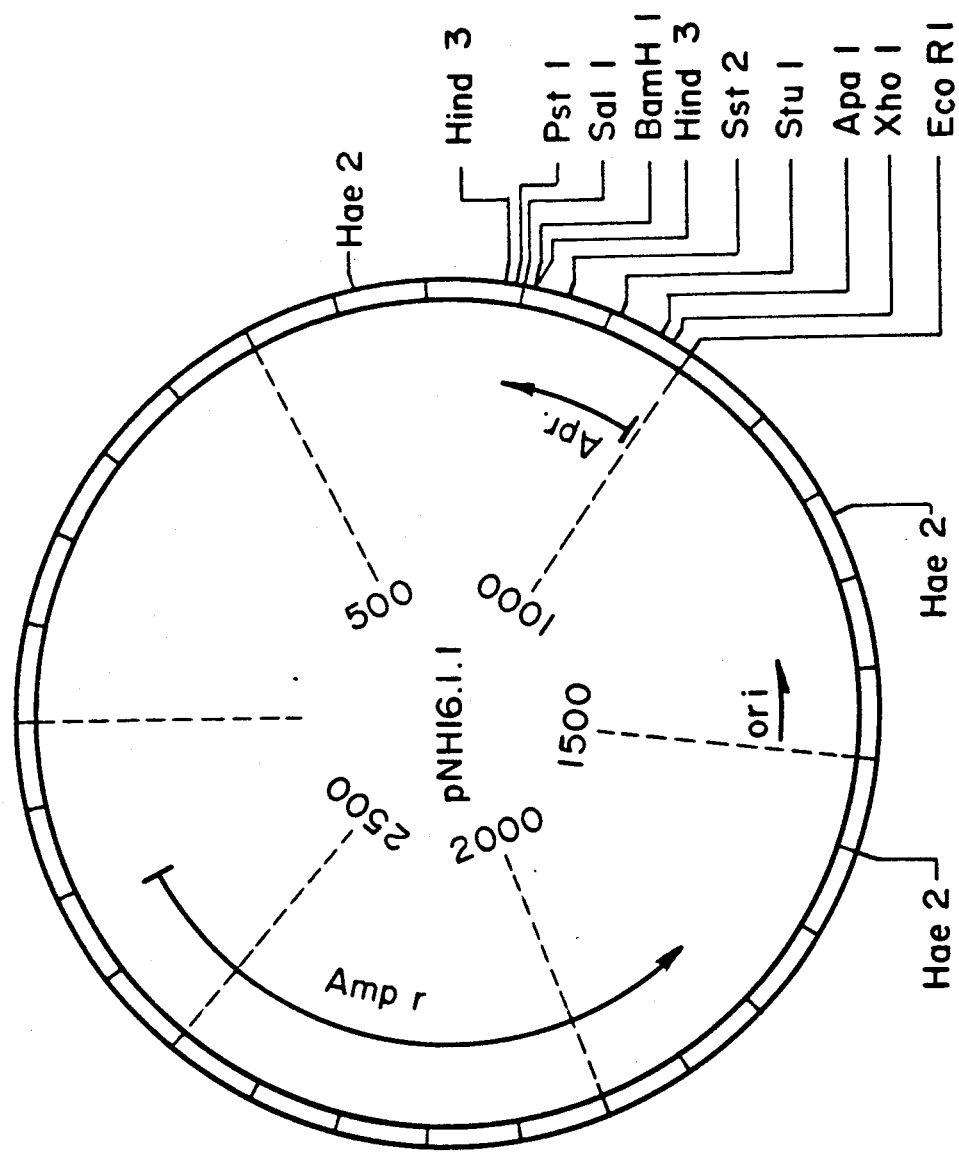
FIG. 6B is a schematic diagram of a restriction map of recombinant plasmid pNH 16.1.1.

Recombinant plasmids pNH 02.1.1.
(Val-15-Leu-17-Glu-52-aprotinin). pNH 16.1.1.
(Val-15-Leu-17-Glu-39-Glu-52-aprotinin) pRK 126.1.24
(Val-15-Leu-17-aprotinin) and pRK 113.1.1.
(Val-15-Leu-17-Thr-52-aprotinin The recombinant plasmid pNH 02.1.1. (FIG. 5) contains a coding region for the synthetic Val-15-Leu-17-Glu-52-aprotinin gene. The recombinant plasmid pNH 16.1.1. (FIG. 6) contains a coding region for the synthetic Val-15-Leu-17-Glu-39-Glu-52-aprotinin gene.

Plasmid pNH 02.1.1. (Val-15-Leu-17-Glu-52-aprotinin) was constructed by exchange of a β-block which is an Apa I-Stu I fragment, containing a codon for Leu at position 17 instead of Arg (see FIG. 7).

About 100 pmol of the synthetic ss DNA fragments β-EA10A and β-EA10B (FIG. 7) were dissolved in 20 μl water, heated for 5 minutes at 95° C. and cooled down slowly to room temperature (5 hours). The hybridized unphosphorylated fragment was ligated with 1.5 pmol purified DNA from pRK 54.1.1 missing the Apa I-Stu I fragment.

Transformation of *E. coli* RRI ΔM15 was performed with 50% of the ligation mixture. From 1500 transformants 24 were tested by analytical plasmid isolation and restriction analysis.

All were positive and two of them were sequenced as described in Material and Methods. The transformant pNH 02.1.1 was used for further experiments.

Plasmid pNH 16.1.1 containing the Val-15-Leu-17-Glu-39-Glu-52-arprotinin gene was constructed by a simple exchange of a γ-block, which is a Stu I-Sst II fragment of pNH 02.1.1 containing a codon for Glu at position 39 instead of Arg.

About 100 pmol of the synthetic ss DNA fragments γ-EA 2A and γ-EA 2B (FIG. 7) were dissolved in 20 μl water, heated for 5 minutes at 95° C. and cooled down slowly to room temperature (5 hours). The hybridized unphosphorylated fragment was ligated with 1.5 pmol purified DNA from pNH 02.1.1 missing the Stu I-Sst II fragment.

Transformation of *E. coli* RRI ΔM15 was done with 50% of the ligation mixture. *E. coli* transformants were tested by analytical plasmid isolation and restriction analysis. A positive clone was sequenced as described in Material and Methods. The transformant pNH 16.1.1 was used for further experiments.

Plasmid pRK 126.1.24 (Val-15-Leu-17-Met-52-aprotinin) was derived from pNH 02.1.1 by exchange of a δ-block containing the codon for threonine at position 52 instead of Glu. About 100 pmol of the synthetic ss DNA fragments δ-EA 1A and δ-EA 1B (FIG. 7) were dissolved in 20 μl water heated for 5 minutes at 95° C. and cooled down slowly to room temperature (5 hours). The hybridized unphosphorylated fragment was ligated with 1.5 pmol purified DNA from pNH 02.1.1 missing the Sst II-Bam HI fragment.

Transformation of *E. coli* RRI ΔM15 was done with 50% of the ligation mixture. *E. coli* transformants were tested by analytical plasmid isolation and restriction analysis. A positive clone was sequenced as described in Material and Methods. The transformant pRK 126.1.24 was used for further experiments.

Plasmid pRK 113.1.1 (Val-15-Leu-17-Thr-52-aprotinin) was derived from pNH 02.1.1 by exchange of a δ-block containing the codon for threonine at position 52 instead of glutaminic acid. About 100 pmol of the synthetic ss DNA fragments δ-EA 7A and δ-EA7B (FIG. 7) were dissolved in 20 μl water heated for 5 minutes at 95° C. and cooled down slowly to room temperature (5 hours). The hybridized unphosphorylated fragment was ligated with 1.5 pmol purified DNA from pNH 02.1.1 missing the SstII/Bam H1 fragment. Transformation of *E. coli* RRI ΔM15 was done with 50% of the ligation mixture. *E. coli* transformants were tested by analytical plasmid isolation and restriction analysis. A positive clone was sequenced as described in Material and Methods. The transformant pRK 113.1.1 was used for further experiments.

EXAMPLE 4

Expression plasmids pES 044.1.1, pES 045.1.3, pNH 05.1.1 and pNH 21.1.1

An example for expression of aprotinin variant genes in E. coli is given by expressing said genes as fusions with the lacZ gene (U. Rüther and B. Müller-Hill (1983), *EMBO Journal*, 2, 1791–1794) or with the N-terminal part pf the RNA polymerase of phage MS-2 (Remault et al (1981), Gene 15, 81–93).

Aprotinin genes obtained from plasmids pNH 02.1.1 (Val-15-Leu-17-Glu-52-aprotinin) and pNH 16.1.1 (Val-15-Leu-17-Glu-39-Glu-52-aprotinin) were ligated into expression plasmid pUR 278 (U. Rüther and B. Müller-Hill (1983), *EMBO Journal*, 2, 1791–1794).

Figure 8:
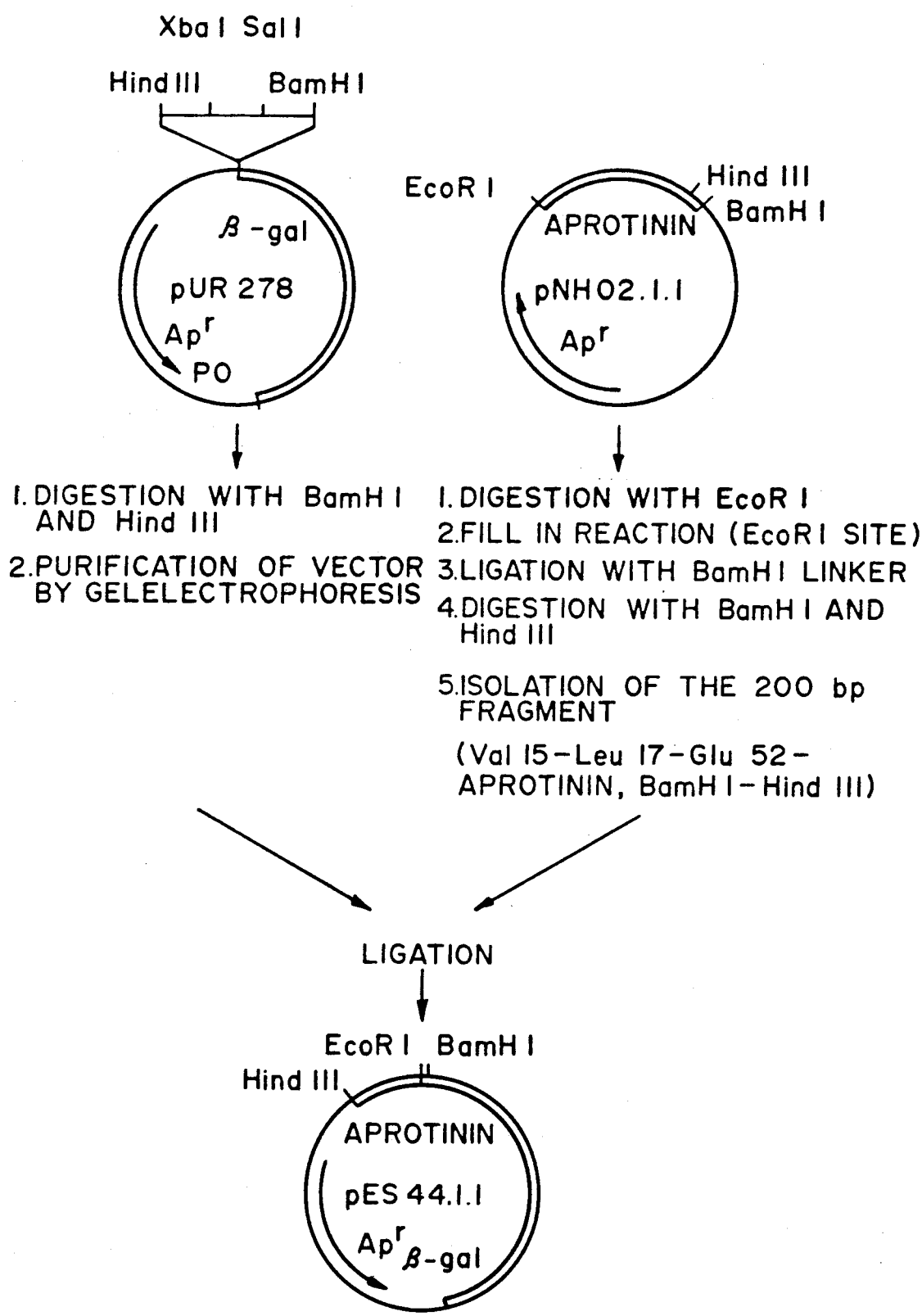
FIG. 8 schematically depicts the construction of expression plasmid pES 44.1.1.

For cloning the synthetic aprotinin gene in expression vector pUR 278 cloning sites Bam HI and Hind III were chosen. Therefore, ist was necessary to modify the aprotinin gene by adding a Bam HI site at the 5'-EcoRI end of the gene and using the Hind III site at the 3'end (see FIG. 8).

5 pmol of the plasmid pNH 02.1.1 was completely digested for 5 hours at 37° C. with EcoRI (1.5 pmol/µl) in 50 µl 1X SP-100.

After digestion the material was phenol extracted, ethanol precipitated and dried under vacuum.

The protruding 5' EcoRI ends of this material were filled enzymatically with DNA polymerase I (Klenow fragment), dATP and TTP.

5 pmol of this DNA were dissolved in 2 µl 10 mM dATP, 2 µl 10 mM TTP, 5 µl 10 x NT-buffer and 39 µl water. Then 2 µl DNA polymerase I (Klenow fragment, 5 units/µl) were added and incubation at room temperature took place (30 minutes). The material was phenol extracted, ethanol precipitated, washed twice with 80% ethanol and dissolved in 20 µl TE-buffer. 20 µl of this material with flush ends were used for ligation with Bam HI linker. Therefore, 200 pmol of phosphorylated Bam HI linker were ligated to 10 pmol DNA ends (standard ligation conditions, 4.5 µl T4 DNA ligase, total colume 60 µl), incubation at 14° C. for 18 hours. The reaction mixture was phenol/sevag extracted, ethanol precipitated, washed, dried and dissolved in 10 µl TE. For preparation of the synthetic aprotinin gene with Bam HI and Hind III termini, the "linkered" linear plasmid (10 pmol) was cut first with Hind III (10.5 pmol hit/µl, 5 h, 37° C.) and than with Bam HI (40 pmol hit/µl, 20 h, 37° C. standard conditions). The fragment was isolated after separation on 1.8% agarose gel electrophoresis and carefully purified (see standard procedure).

VECTOR PREPARATION

The parental vector pUR 278 (about 5 pmol) was cut first with Hind III (standard conditions) purified by phenol/sevag extraction, ethanol precipitation, redissolved and then digested with Bam HI (standard conditions). This material was loaded on a 1% agarose gel, electrophorized, isolated and purified according to the standard conditions, to get rid of the 18 base pair long Bam HI-Hind III fragment which would compete in ligation with the synthetic aprotinin gene.

LIGATION AND TRANSFORMATION

For ligation 0.3 pmol vector, 1.5 pmol fragment (approximately), 2 units T4-DNA ligase were used (standard conditions, total volume 30 µl, incubation 4 hour at 14° C.). Transformation was performed with E.coli strain RRI delta M15 as host using one third of the ligation mixture (standard condistions). A total of 173 "blue" colonies were received on indicator plates containing 200 µg ampicillin/ml. From this 12 transformants were analyzed further by rapid analytical plasmid isolation (standard conditions). Of 173 transformants 30 should be background transformants, calculated on the percentage of transformants received by religation of vector. This result was confirmed by restriction analysis of plasmids of the 12 transformants. 8 of them were positive showing a Bam HI-Hind III restriction fragment of about 200 base pairs. Positive recombinant plasmids were also linearized by Sst II a unique restriction site within the aprotinin gene. Base sequence analysis according to the standard procedure as described in Material and Methods. Revealed that the plasmid pES 44.1.1 had inserted the desired aprotinin DNA fragment (see FIG. 8). Plasmid pES 44.1.1 was used for further analysis and expression work. The construction of plasmid pES 45.1.3 was done by exact the same procedure using the Val-15-Leu-17-Glu-39-Glu-52-aprotinin gene from pNH 16.1.1. The positive recombinant plasmid pES 45.1.3 showed the correct DNA sequence and this construction was used for further analysis and expression work.

Figure 9:
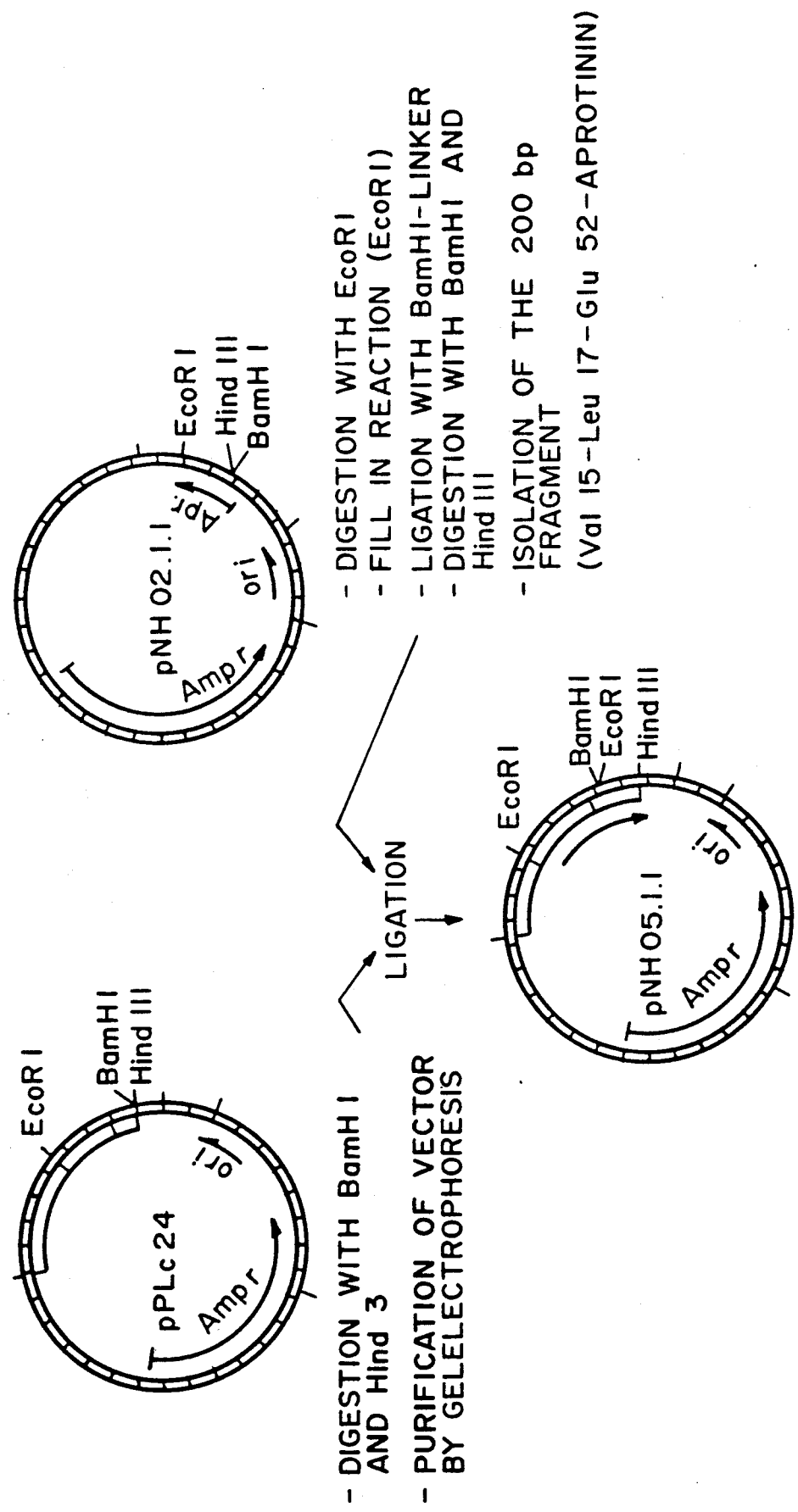
FIG. 9 schematically depicts the construction of expression plasmid pNH 05.1.1.

The construction of plasmids pNH 05.1.1 (Val-15-Leu-17-Glu-52-aprotinin (see FIG. 9) and pNH 21.1.1 (Val-15-Leu-17-Glu-39-Glu-52-aprotinin) was done by using the procedure shown in FIG. 9. The Val-15-Leu-17-Glu-52-aprotinin gene was obtained from pNH 02.1.1 as EcoRI-Hind III fragment. For cloning into expression vector pPLc 24 it was necessary to modify the aprotinin gene by adding a Bam HI site at the 5'-EcoRI end of the gene. This was done as described above for cloning the gene into pUR278. The modified gene was inserted into vector pPLc 24 which had been restricted with Bam HI and Hind III. In this construction the aprotinin gene is connected in frame to the N-terminal part of the RNA polymerase of phage MS-2 (Remault et al., *Gene*, 15, 81–93 (1981). Plasmid pNH 05.1.1 was used for further analysis and expression.

Plasmid pNH 21.1.1 was prepared in the same way as for pNH 05.1.1 by ligating the modified EcoRI/Hind III fragment obtained from plasmid pNH 16.1.1 into plasmid pPL 24 which had been restricted with Bam HI and Hind III.

EXAMPLE 5

Construction of the α-amylase secretion vector pCH 2742

Figure 10:
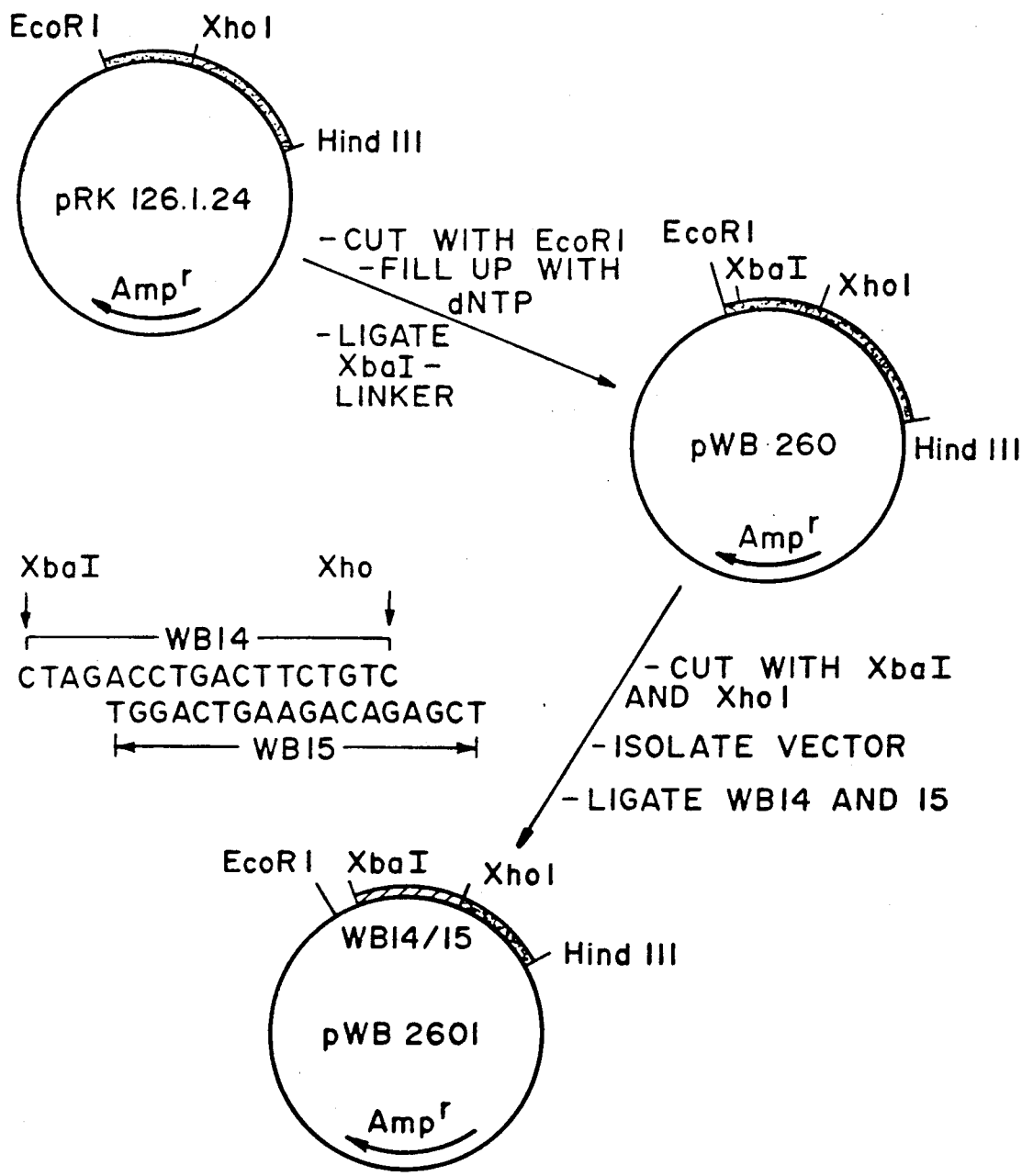
FIG. 10 schematically depicts the construction of vector pWB 2601.

For the cloning into the E.coli secretion vector pCH 237 the gene for Val-15-Leu-17-Met-52-aprotinin was modified by introducing a Xba I-site at the codon for Arg-1. For this purpose pRK 126.1.24 was restricted at EcoRI and after fill up with dNTP in the presence of DNA polymerase (large fragment) a XbaI linker (Biolabs 1010) was ligated into the restriction site (see FIG. 10) leading to pWB 260. pWB 260 was restricted at XbaI and XhoI, the vector was isolated and a linker consisting of two synthetic DNA fragments (WB 14 and WB 15) was ligated into pWB 260 leading to pWB 2601 (FIG. 10).

Figure 11B:
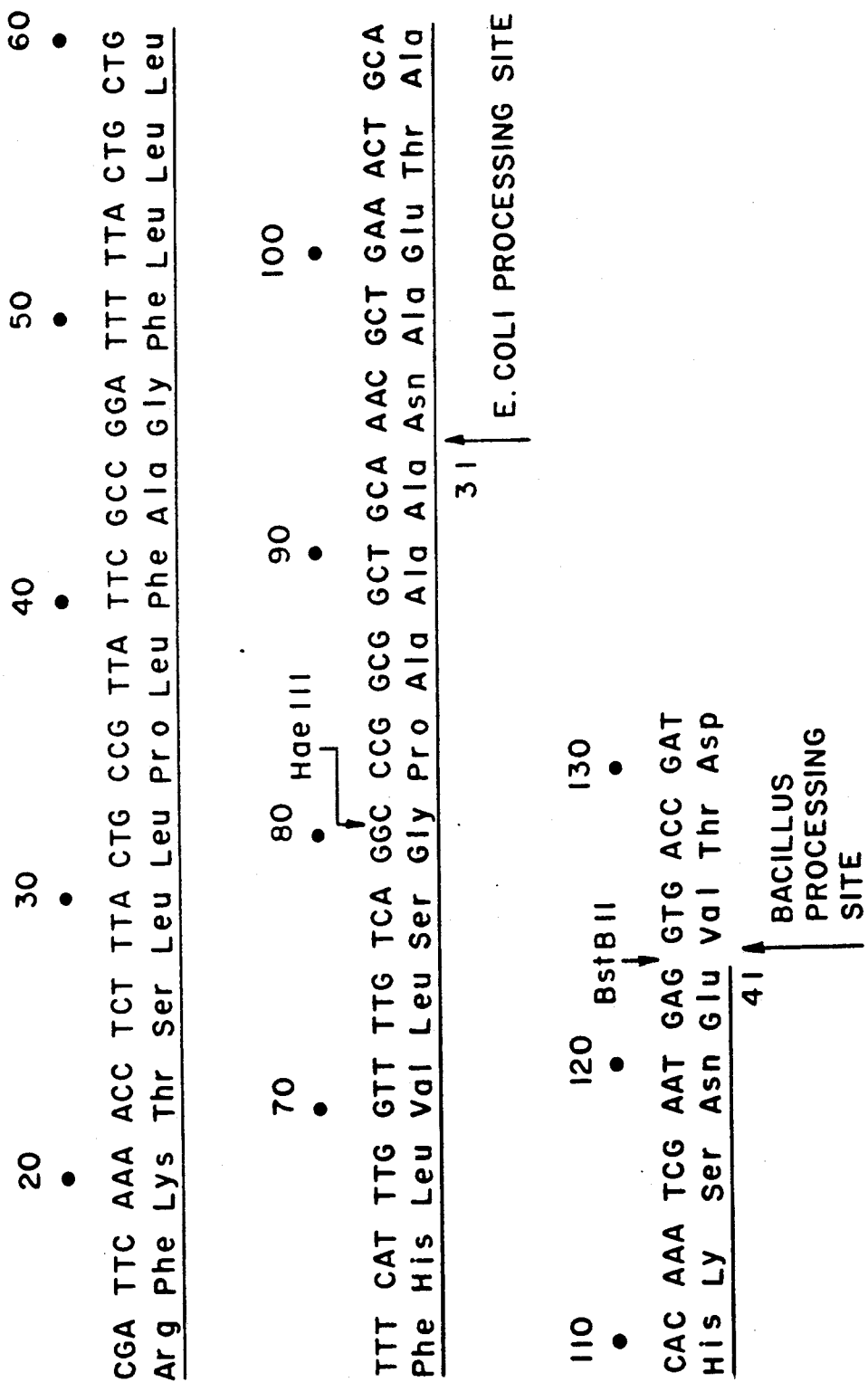
FIG. 11 depicts a DNA sequence of an alpha-amylase leader from plasmid pALK1.

Construction of the α-amylase secretion vector was carried out as follows:

The α-amylase signal sequence from B.subtilis was derived from *Bacillus subtilis* DSM 704 (Deutsche Stammsammlung für Mikroorganismen, Göttingen) by cloning a partial Sau3A digest of chromosonal DNA into the BamHI site of pMK 3 (M. A. Sullivan et al. (1984), Gene, 29, 21-26). One of the clones containing a 3 Kb DNA fragment with the α-amylase gene was modified by deletion of parts of the α-amylase structural gene in order to yield pALK1. DNA Sequences of pALK1 revealed a possible ribosome binding site (RBS) and a signal sequence on a 230 bp EcoRI-BstEII fragment with extensive homology to an α-amylase from B.subtilis 1A289 (compare DNA sequence in FIG. 11 with M. Yang et al. (1983), Nucleic Acid Research, 11, 237-249). Since processing of the α-amylase signal sequence in E.coli occurred after amino acid position 31 a NheI-restriction site was introduced at ala 31. For this purpose was isolated from pALL1 a 180 bp EcoRI-HaeIII fragment containing the possible Shine-Dalgarno site and a large part of the signal sequence of α-amylase (fragment A in FIG. 12). Fragment B (see FIG. 12), a synthetic linker which generates the NheI-site at codon 31 of the amylase signal sequence was ligated together with fragment A (see FIG. 12) into pBR 322 cut with EcoRI and NheI (pWB 226). pWB 226 was restricted at BamHI, and after fill up with dNTP a HindIII-linker (Biolabs 1002) was ligated into the vector leading to pWB 2024.

Figure 12A:
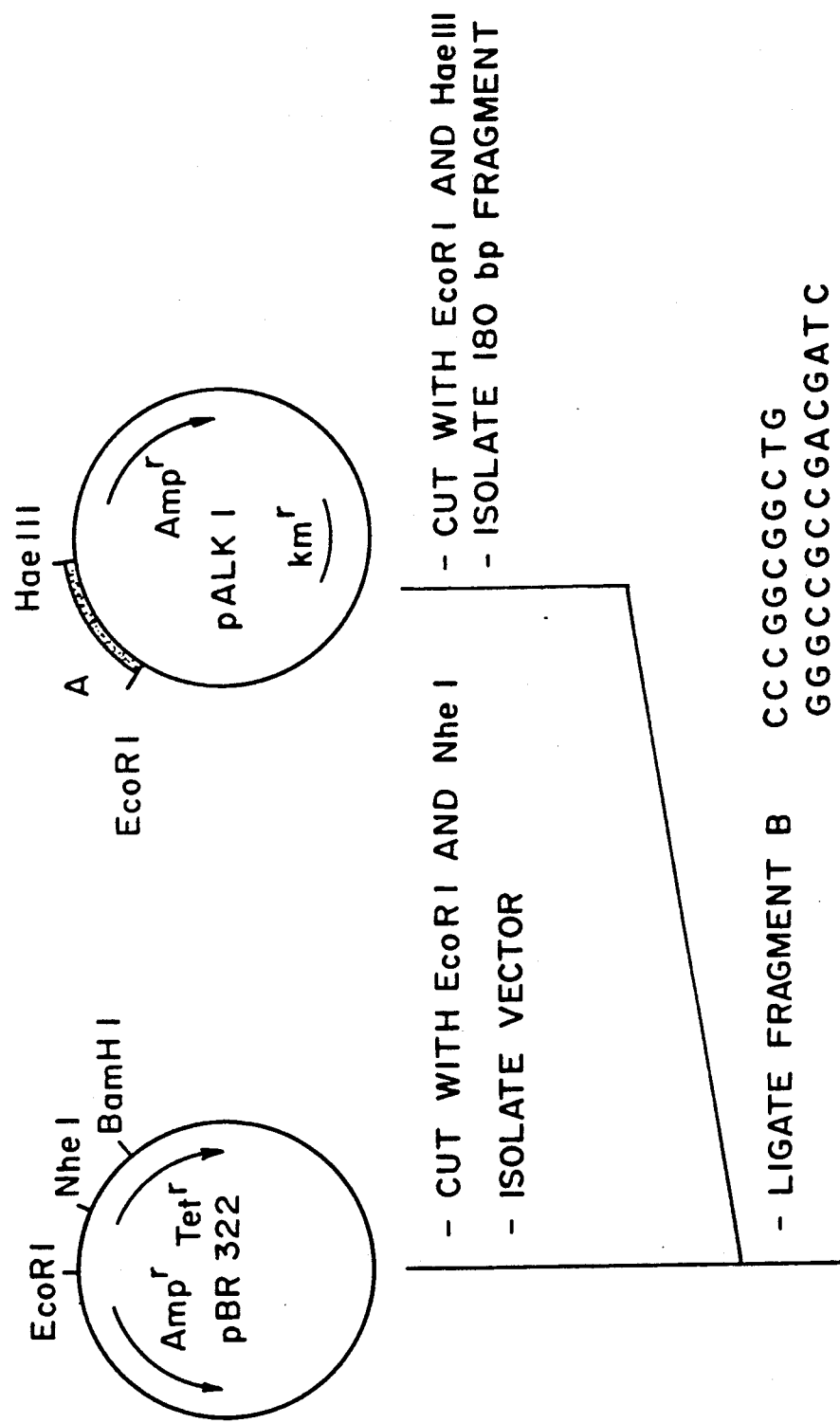
FIG. 12 schematically depicts construction of plasmid pCH 237.
Figure 12B:
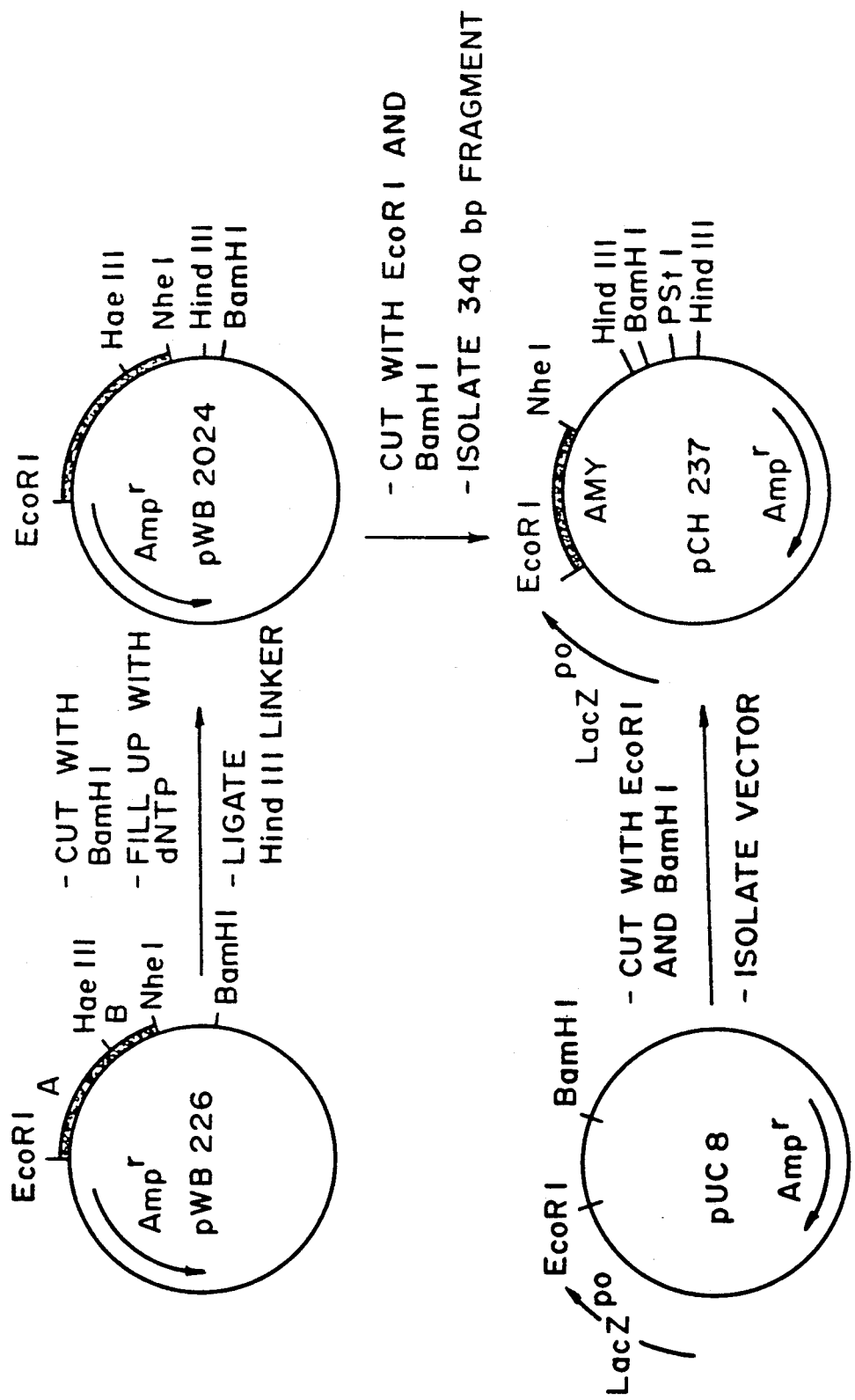

The secretion vector pCH 237 was constructed by moving the amylase signal sequence behind the lacZ promoter in pUC 8 (FIG. 12). In this construction the reading frame of lacZ' should be terminated at the TAA-stop codon (pos. -58/-56 in the DNA sequence of fragment A, FIG. 11). Reinitiation of protein synthesis on the same mRNA should take place after binding of the ribosome to the possible Shine-Dalgarno site of α-amylase about 50 bases downstream from the stop codon at position-10.

Figure 13:
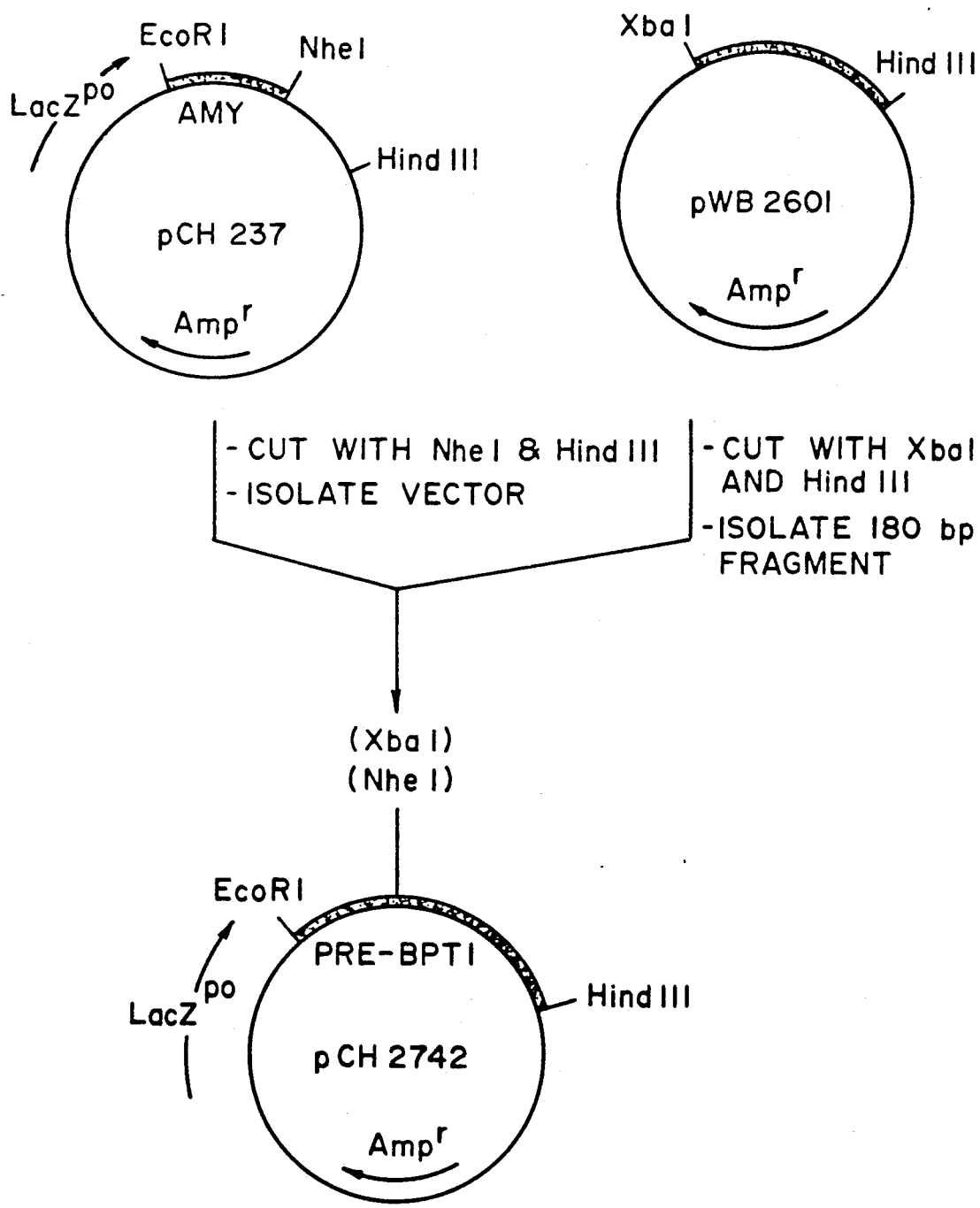
FIG. 13 schematically depicts construction of plasmid pCH 2472.

For the expression of Val-15-Leu-17-Met-52-aprotinin the aprotinin gene was isolated as XbaI-HindIII fragment from pWB 2601 and integrated behind the α-amylase signal sequence in pCH 237, restricted with NheI and HindIII, leading to pCH 2472 (FIG. 13).

EXAMPLE 6

Isolation of an
MS-2-Val-15-Leu-17-Glu-39-Glu-52-aprotinin and/or
an MS-2-Val-15-Leu-17-Glu-52-aprotinin fusion protein
expressed in E. coli To attempt expression of MS-2-aprotinin fusion proteins E. coli C600 [pcI 857] transformed with plasmid pNH 05.1.1 or pNH 21.1.1 was cultivated in a broth containing 30 g/l yeast extract, 30 g/l beef extract, and 1 g/l K$_2$HPO$_4$ in deionized water. The pH was adjusted to 7.0. 100 ml of the broth was placed into 1 l Erlenmeyer flasks and autoclaved at 121° C. for 20 minutes. After incubation with a seed culture cultivated in the same medium at 28° C. for 8 hours the flasks were incubated on a rotary shaker at 280 rpm (diameter of shaking movement: 5 cm) for 4 hours at 28° C. By that time the optical density of the culture was about 4 (measured at 700 nm). The temperature was then increased to 42° C. and the incubation continued for another 3 hours. By that time the cells contained fusion protein amounting to about 15% of total cell protein. The fusion protein could be visualized by standard polyacrylamide gel electrophoresis using 17% acrylamide concentration and staining with coomassie blue.

Heat-induced cells were collected from the culture broth by centrifugation for 15 minutes at 5000 rpm (Beckman JA-10), resuspended in 10 ml/g wet weight buffer A (0.1M Tris-HCl, pH 7.5 containing 10 mM EDTA, 5 mM β-mercaptoethanol and 5 mM benzamidine-HCl) and incubated for 30 minutes at 30° C. with 0.2 mg/ml lysozyme (about 100.000 units/mg. Fluka AG, Switzerland) under vigorous stirring.

The suspension was then cooled to 4° C. and passed twice through a french pressure cell (Aminco, USA) at 18000 psi to disrupt the cell membranes. Insoluble material was recovered by centrifugation for 30 minutes at 10000 rpm (Beckman Ja-10) and the supernatant discarded.

The pellet was resuspended and centrifuged as described above twice in buffer A to which 2M urea had been added. The supernatants were again discarded.

The pellet was then dissolved in 10 ml/g wet weight buffer B (0.05 M Tris-HCl pH 8.5 containing 8M guanidine-HCl and 10 mM β-mercaptoethanol), the solution clarified by centrifugation for 30 min at 18000 rpm (Beckmann JA-20) and 10 ml loaded onto a column (5 × 90 cm) filled with Sephacryl S-300 (Pharmacia AB, Sweden) equilibrated in buffer C (0.05M Tris-HCl pH 8.5 containing 6M urea and 10 mM β-mercaptoethanol). Fractions of 10 ml were collected and the peak containing the fusion protein identified by SDS-PAGE under reducing conditions. Peak fractions were combined and dialyzed exhaustively against water. Under these conditions the fusion protein precipitated and was collected by centrifugation for 30 minutes at 10.000 rpm (Beckman JA-10). Fusion protein pellets were stored at −70° C.

Figure 14:
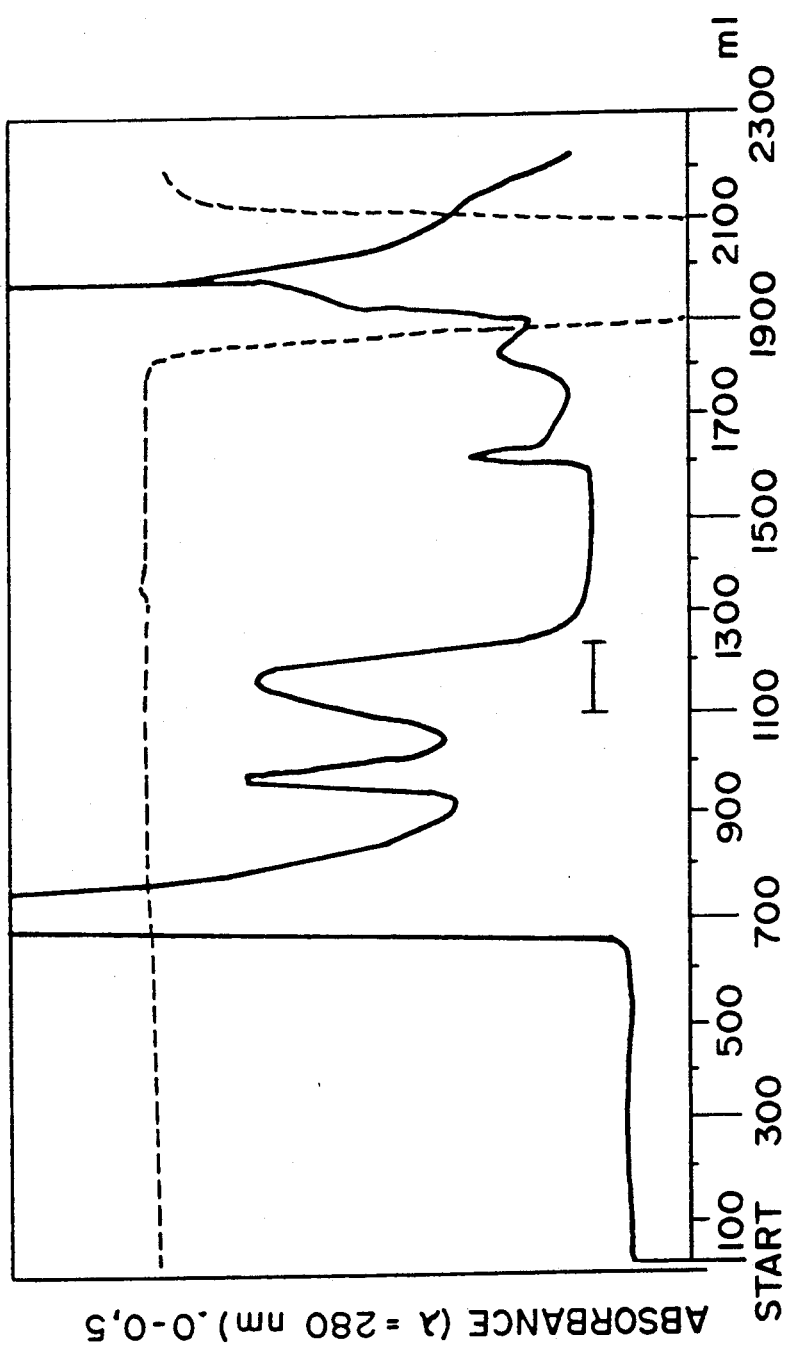
FIG. 14 is a graph depicting the results of purification of a MS2-Val-15-Leu-17-Glu-52-aprotinin fusion protein by gelfiltration.

FIG. 14 shows a typical separation. Fractions containing the fusion protein are indicated by a bar.

EXAMPLE 7

Preparation of bioactive
Val-15-Leu-17-Glu-52-aprotinin from purified
MS-2-fusion protein Fusion protein (as prepared according to example 6) was dissolved in about 5 ml/100 mg wet weight 70% formic acid and ticated with cyanogen bromide (ratio methionine:CNBr = 1:250) for 18 hours under nitrogen at room temperature (Witkop et al. (1968), Science, 162, 318-326). The cleavage mixture was then diluted 10- to 20-fold with water and the formic acid and residual CNBr removed under reduced pressure.

The concentrated solution was titrated to pH 7.5 with 5M NaOH and solid urea added to a final concentration of 8 molar. After addition of 25 mM β-mercaptoethanol and incubation for 2 hours at 37° C. under nitrogen the solution was dialyzed overnight against 20 volumes buffer D (0.05M Na-acetate pH 5.2 containing 6M urea and 10 mM β-mercaptoethanol) at 8° C.

Figure 15:
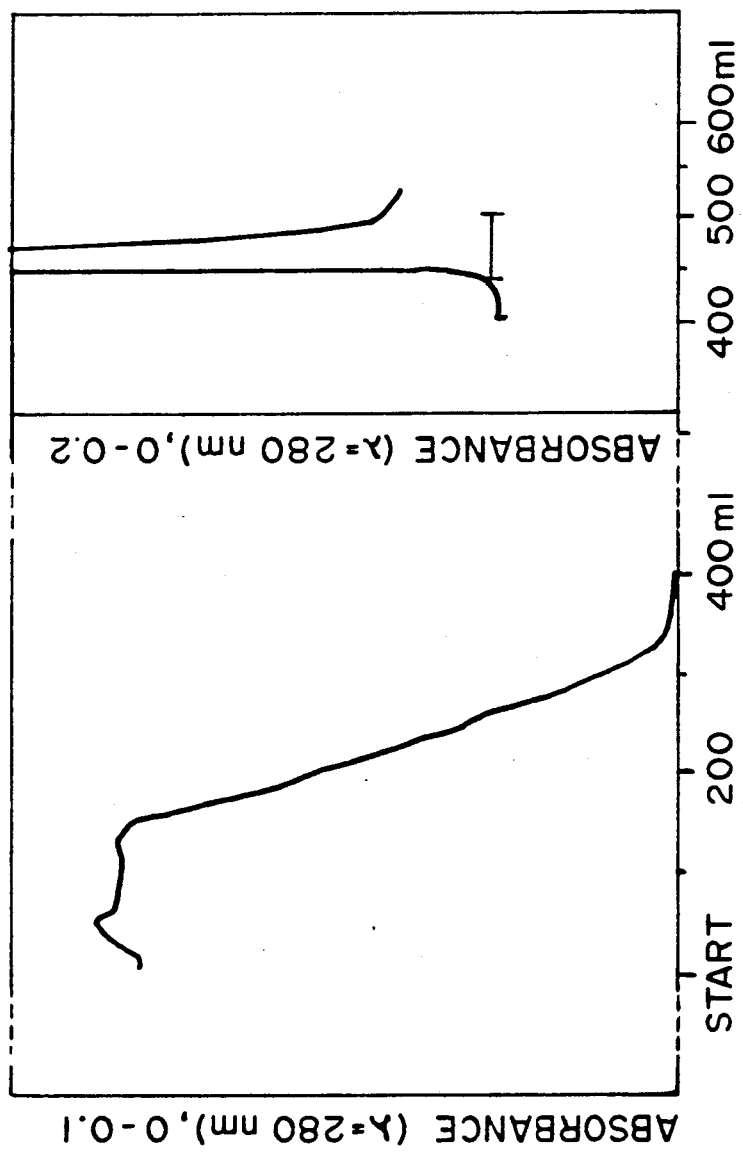
FIG. 15 is a plot depicting the results of the renaturation of Val-15-Leu-17-Glu-52-aprotinin on "CM-SEPHAROSE".

To renature Val-15-Leu-17-Glu-52-aprotinin the solution was loaded onto a column (2.5 × 5 cm) filled with CM-Sepharose fast flow (Pharmacia AB, Sweden) equilibrated in buffer D. The column was washed with buffer D (about 8-10 column volumes) and developed with a linear gradient formed between 150 ml buffer D and 150 ml buffer E (0.05M Na-acetate, pH 5.2, containing 2 mM β-mercaptoethanol) followed by a short wash with 0.05M Na-acetate pH 5.2 (about 2 to 3 column volumes). Finally renatured Val-15-Leu-17-Glu-52-aprotinin was eluted with 0.05M Na-acetate pH 5.2 containing 0.5M NaCl (see FIG. 15).

Figure 16:
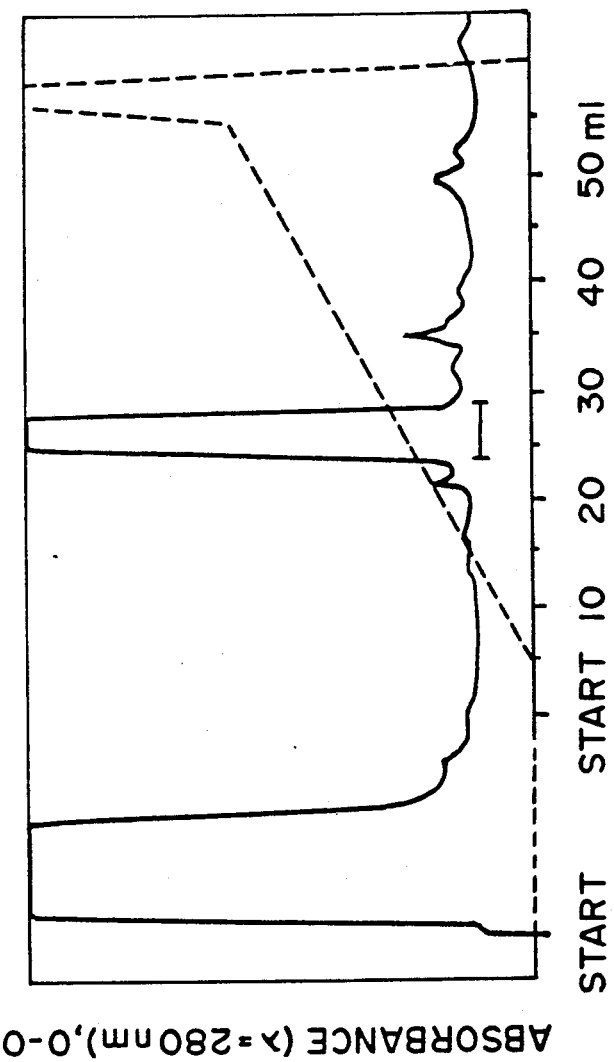
FIG. 16 is a plot depicting the results of the purification of Val-15-Leu-17-Glu-52-aprotinin on a "MONO S" column.

Peak fractions of the NaCl-eluate (as indentified by SDS-PAGE) were collected and dialyzed exhaustively against 20 mM Hepes pH 6.5 to allow further purification on a Mono S column (1 ml) equilibrated in the same buffer (FPLC, Pharmacia, Sweden). Protein was bound to the column and eluted within a linear gradient of zero to 300 mM NaCl (see FIG. 16). Peak fractions containing the aprotinin variant were collected, dialyzed exhaustively against 0.1M ammonium bicarbonate and lyophilized in suitable aliquots.

usually 0.5-1.5 mg purified Val-15-Leu-17-Glu-52-aprotinin was recovered per liter of culture broth.

Figure 17A:
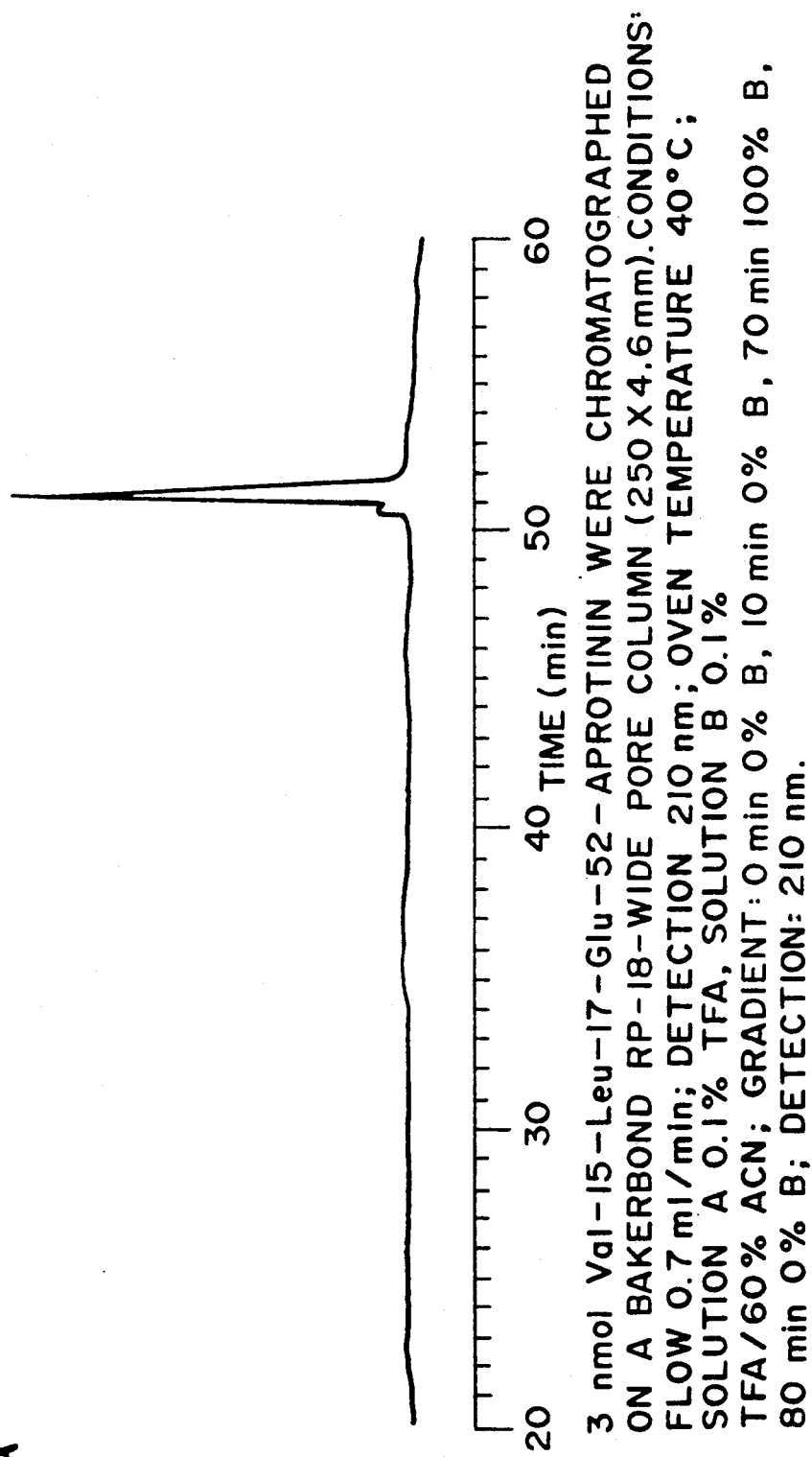
FIG. 17A is a plot depicting the results for HPLC-chromatography of Val-15-Leu-17-Glu-52-aprotinin.

The purified protein had the expected characteristics as far as amino acid composition, linear sequence (pos. 1-25), molecular weight and behaviour on reversed phase HPLC (FIG. 17) was concerned (see Example 9).

EXAMPLE 8

Isolation of Val-15-Leu-17-aprotinin expressed in *E. coli* RRI ΔM15 pCH 2742

*E. coli* RRI ΔM15 transformed with pWB 2742 was grown as overnight cultures. The medium contained 3% beef extract (Gibco), 1.5% yeast extract (Gibco), 0.5% K$_2$HPO$_4$ and 4% morpholino ethane sulfonic acid, dissolved in distilled water. The pH-value was adjusted to 7.0. 100 ml of the medium were placed into 1 l Erlenmeyer flasks and autoclaved for 20 minutes at 121° C. After cooling ampicillin, which had been dissolved in distilled water and sterilized by filtration, was added to a final concentration of 50 µg/ml. For the production of Val-15-Leu-17-aprotinin the flasks were inoculated with 1 ml of an overnight culture grown in the same medium at 28° C. The flasks were incubated on a rotary shaker at 280 rpm at 28° C. for 3 hours until the optical density measured at 550 nm was about 1. At that time induction of the lac promoter was done by adding 1 mM isopropylthiogalactosid (Sigma) to the cultures. Fermentation was continued for 20 hours and cells were harvested by centrifugation at 8000 rpm (10 minutes 4° C. in a Kontron Centrikon H-401 with rotor A 6.14).

Cells were homogenized in 500 ml 0.01M Tris buffer pH 8.0, and broken by ultra sonication under cooling with crunched ice at 400 W until more than 95% of all cells had been disrupted. 30 ml perchloric acid (72%) were added to this suspension (700 ml) under stirring. After 30 minutes the supernatant was recovered by centrifugation (20 min/6000 rmp). It was neutralized by the addition of saturated Tris base solution and passed over a 50 ml gel bed anti-aprotinin antibodies (raised in rabbits against aprotinin) immobilized on Sepharose CL 4B by the BrCN method. No active material was found in the effluent. The gel was washed successively with 0.2 Tris buffer pH 8.0, and water, whereby no activity was desorbed. Activity could be desorbed by elution with 0.2M acetic acid, adjusted to pH 1.9 with HCl. This eluate was lyophilized and redissolved in 5 ml 0.02M Hepes buffer pH 6.0. Further purification was achieved by FPLC on Mono S ® (Pharmacia, Sweden) using an increasing gradient of NaCl (0-0.5M). Activity was found in fractions 41-47 (see FIG. 18), which were pooled, dialyzed and lyophilized.

EXAMPLE 9

Protein chemical characterization of Val-15-Leu-17-aprotinin variants

Total amino acid analysis was carried out as described in Materials and Methods. The result obtained regarding the amino acid composition of
Val-15-Leu-17-Glu-52-aprotinin,
Val-15-Leu-17-Thr-52-aprotinin,
Leu-15-Leu-17-Glu-52-aprotinin,
Val-15-Leu-17-Glu-39-Glu-52-aprotinin, and
Val-15-Leu-17-Met-52-aprotinin
was as follows:

| Amino acid | 1* | 2* | 3* | 4* | 5* |
|---|---|---|---|---|---|
| Asp | 5.09(5) | 5.18(5) | 5.15(5) | 4.95(5) | 5.13(5) |
| Thr | 3.03(3) | 3.89(4) | 2.83(3) | 2.81(3) | 2.87(3) |
| Ser | 1.19(1) | 1.13(1) | 1.02(1) | 1.15(1) | 1.01(1) |
| Glu | 4.43(4) | 3.31(3) | 4.44(4) | 5.57(5) | 3.20(3) |
| Ala | 6.00(6) | 6.00(6) | 6.00(6) | 5.84(6) | 6.31(6) |
| Gly | 6.28(6) | 5.86(6) | 5.84(6) | 5.92(6) | 6.02(6) |
| Val | 2.13(2) | 1.97(2) | 0.98(1) | 2.00(2) | 1.87(2) |
| Met | —(—) | —(—) | —(—) | —(—) | 0.88(1) |
| Ile | 1.45(2) | 1.35(2) | 1.39(2) | 1.42(2) | 1.28(2) |
| Leu | 2.97(3) | 2.87(2) | 3.87(4) | 2.89(3) | 2.90(3) |
| Tyr | 3.73(4) | 3.64(4) | 3.73(4) | 3.09(4) | 3.58(4) |
| Phe | 3.83(4) | 3.83(4) | 3.83(4) | 3.69(4) | 3.83(4) |
| Lys | 2.84(3) | 2.79(3) | 2.92(3) | 2.95(3) | 2.80(3) |
| Arg | 4.82(5) | 4.76(5) | 4.95(5) | 3.79(4) | 4.77(5) |

1* Val-15-Leu-17-Glu-52-aprotinin
2* Val-15-Leu-17-Thr-52-aprotinin
3* Leu-15-Leu-17-Glu-52-aprotinin
4* Val-15-Leu-17-Glu-39-Glu-52-aprotinin
5* Val-15-Leu-17-Met-52-aprotinin Cys and Pro were not determined.

The N-terminal amino acid sequence was determined as described in Materials and Methods. The amino acid sequence obtained after 25 cycles was as follows:

Val-15-Leu-17-Glu-52-aprotinin:
1
Arg—Pro—Asp—Phe—Cys—Leu—Glu—Pro—Pro—Tyr—Thr—Gly—Pro—Cys—Val—

17  18                          25
—Ala—Leu—Ile—Ile—Arg—Tyr—Phe—Tyr—Asn—Ala—

Val-15-Leu-Thr-52-aprotinin
1
Arg—Pro—Asp—Phe—Cys—Leu—Glu—Pro—Pro—Tyr—Thr—Gly—Pro—Cys—Val—

17  18                          25
Ala—Leu—Ile—Ile—Arg—Tyr—Phe—Tyr—Asn—Ala—

Leu-15-Leu-17-Glu-52-aprotinin
1
Arg—Pro—Asp—Phe—Cys—Leu—Glu—Pro—Pro—Tyr—Thr—Gly—Pro—Cys—Leu—

17  18                          25
—Ala—Leu—Ile—Ile—Arg—Tyr—Phe—Tyr—Asn—Ala—

Val-15-Leu-17-Glu-39-Glu-52-aprotinin

-continued

Arg—Pro—Asp—Phe—Cys—Leu—Glu—Pro—Pro—Tyr—Thr—Gly—Pro—Cys—Val—

17  18                              25
—Ala—Leu—Ile—Ile—Arg—Tyr—Phe—Tyr—Asn—Ala—

Val-15-Leu-17-Met-52-aprotinin

Arg—Pro—Asp—Phe—Cys—Leu—Glu—Pro—Pro—Tyr—Thr—Gly—Pro—Cys—Val—

17  18                              25
—Ala—Leu—Ile—Ile—Arg—Tyr—Phe—Tyr—Asn—Ala—

About 30% of the Val-15-Leu-17-Met-52-aprotinin obtained by fermentation of *E.coli* RRI M15 pCH 2742 contained an additional Ala-residue at the N-terminus. This can be avoided by replacing Ala-30 in the α-amalyse signal sequence (see FIG. 11) by Gln.

EXAMPLE 10

Figure 18:
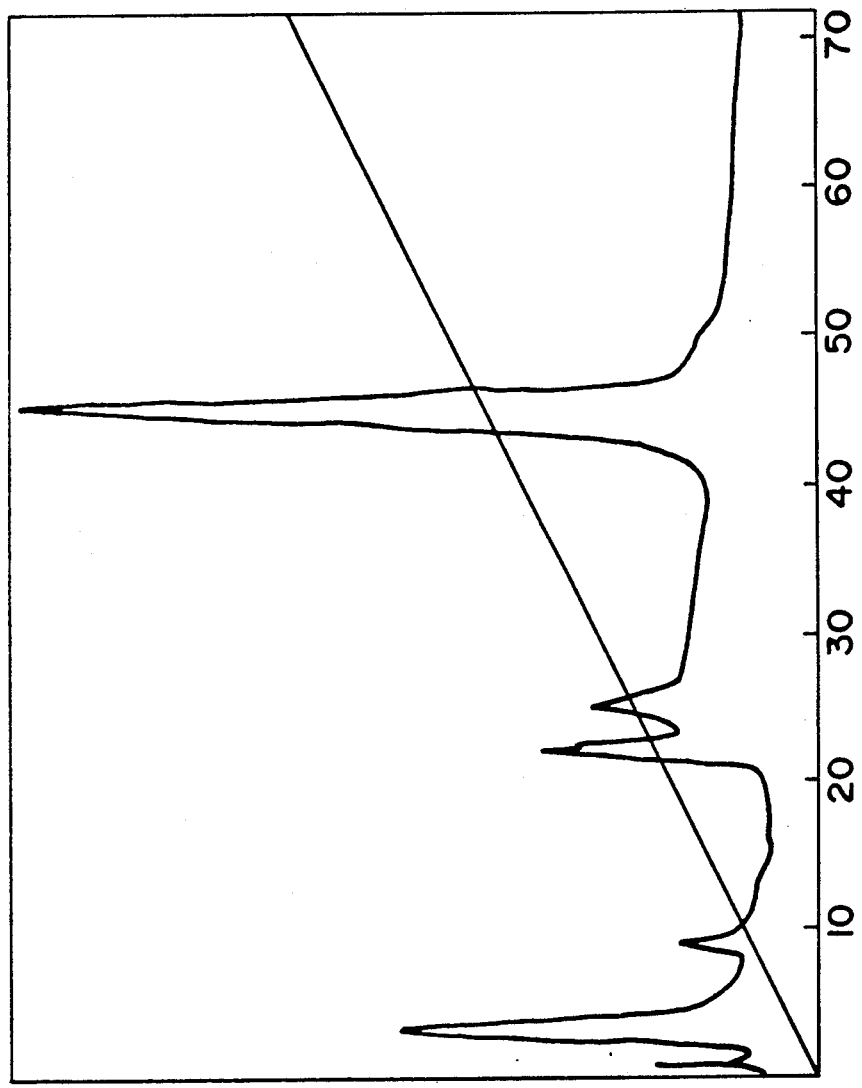
FIG. 18 is a plot depicting the results of a chromatography of Val-15-Leu-17-aprotinin on a "MONO S" column.
Figure 19:
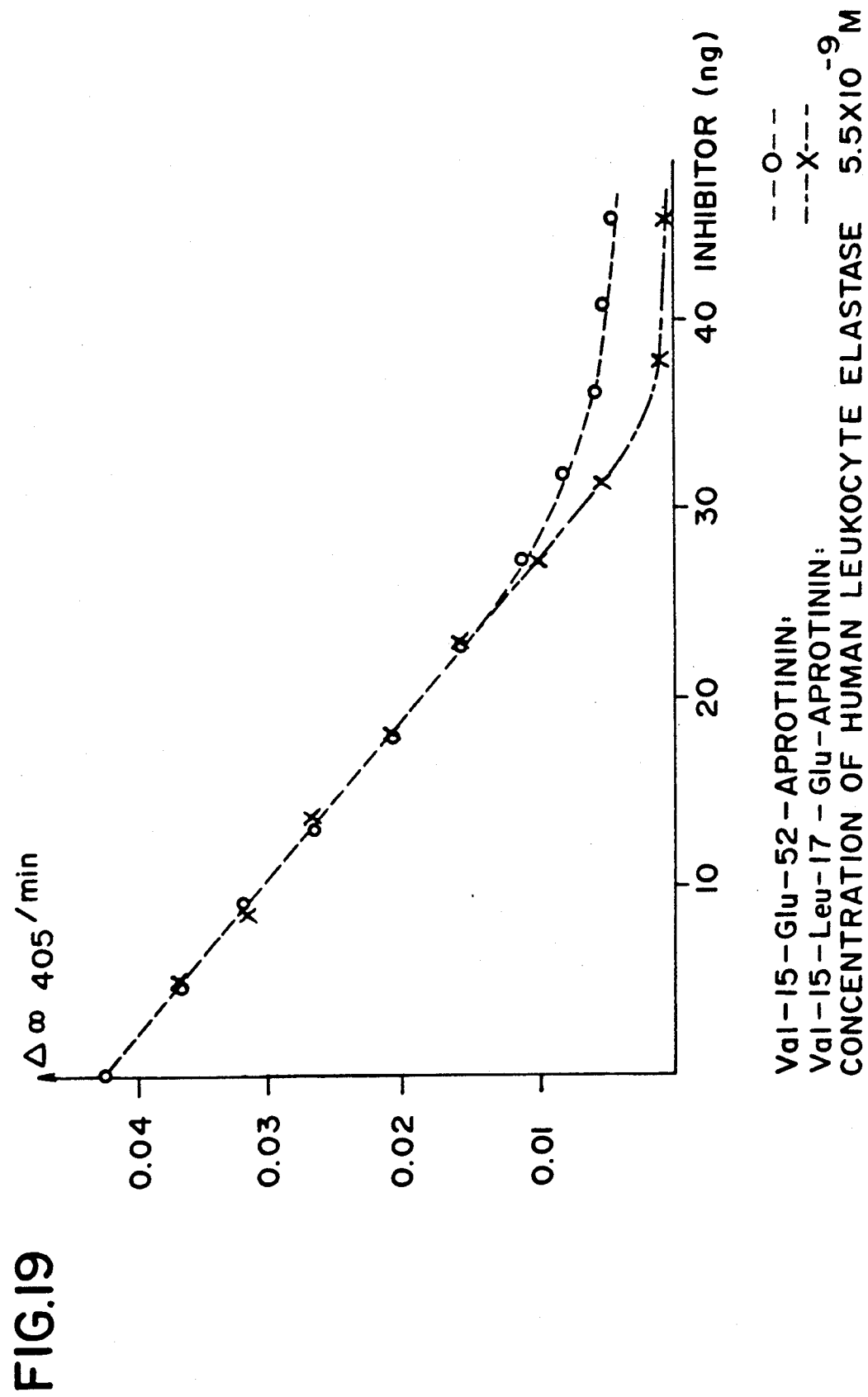
FIG. 19 is a plot depicting the inhibition of human leukocyte elastase by increasing amounts of Val-15-Glu-52-aprotinin and Val-15-Leu-17-Glu-52-aprotinin.

Determination of kinetic constants of Val-15-Leu-17-aprotinin variants $K_i$-values were determined as described in Materials and Methods. The inhibition of human leukocyte elastase (HLE) by increasing amounts of Val-15-Glu-52- and Val-15-Leu-17-Glu-52-aprotinin is shown in FIG. 18. Typical $K_i$-values for the inhibition of human leukocyte elastase, human pancreatic elastase I and human cathepsin G obtained with aprotinin variants were as follows:

|  | $K_i$ (M) | | |
|---|---|---|---|
|  | Human leukocyte elastase | Human pancreatic elastase I | Human Cathepsin G |
| Val-15-Glu-52 | $1.5 \cdot 10^{-10}$ | — | — |
| Val-15-Leu-17-Glu-52 | $5-6 \cdot 10^{-11}$ | $>10^{-6}$ | — |
| Val-15-Leu-17-Glu-39-Thr-52 | $2 \cdot 10^{-11}$ | $5 \cdot 10^{-6}$ | — |
| Val-15-Leu-17-Met-52 | $6 \cdot 10^{-11}$ | $>10^{-6}$ | — |
| Val-15-Leu-17-Thr-52 | $7 \cdot 10^{-11}$ | $>10^{-6}$ | — |
| Leu-15-Leu-17-Glu-52 | $1 \cdot 10^{-10}$ | $>10^{-7}$ | $2 \cdot 10^{-5}$ |
| Leu-15-Leu-17-Glu-39-Glu-52 | $2 \cdot 10^{-9}$ | $1 \cdot 10^{-6}$ | $1 \cdot 10^{-6}$ |

It will be appreciated that the instant specification and claims are set forth by way of illustration and not limitation, and that various modifications and changes may be made without departing from the spirit and scope of the present invention.

What is claimed is:

1. A peptide having essentially the sequence of aprotinin, but comprising in
   position 15 an amino acid selected from the group consisting of Val, Leu and Ile,
   position 17 an amino acid selected from the group consisting of Leu, Arg, Ile and Val,
   position 39 an amino acid selected from the group consisting of Glu and Arg and in
   position 52 an amino acid selected from the group consisting of Met, Thr and Glu except
   a) aprotinin having a replacement only in the 15 position by any of the amino acids Val, Leu, or Ile,
   b) aprotinin having in addition to a replacement in position 15 as described under a) an additional replacement in position 52 by any of the amino acids Glu or Thr,
   c) aprotinin variants as described under a) and b) with an additional Met preceding the N-terminal amino acid Arg-1, and
   d) Val-15-Ser-16-Ile-17-aprotinin.

2. A peptide having essentially the sequence of aprotinin, but comprising in
   position 15 an amino acid selected from the group consisting of Val and Leu,
   position 17 amino acid selected from the group consisting of Leu and Arg,
   position 39 an amino acid selected from the group consisting of Glu and Arg and in
   position 52 an amino acid selected from the group consisting of Met, Thr and Glu except
   a) aprotinin having replacement only in the 15 position by any of the amino acids Val, Leu, or Ile,
   b) aprotinin having in addition to a replacement in position 15 as described under a) an additional replacement in position 52 by any of the amino acids Glu or Thr,
   c) aprotinin variants as described under a) and b) with an additional Met preceding the N-terminal amino acid Arg-1, and
   d) Val-15-Ser-16-Ile-17-aprotinin.

3. A peptide having essentially the sequence of aprotinin, but said peptide selected from the group consisting of
   Val-15-Leu-17-aprotinin,
   Val-15-Leu-17-Glu-52-aprotinin,
   Val-15-Leu-17-Thr-52-aprotinin,
   Val-15-Leu-17-Glu-39-aprotinin,
   Val-15-Leu-17-Glu-39-Glu-52-aprotinin,
   Val-15-Leu-17-Glu-39-Thr-52-aprotinin,
   Leu-15-Leu-17-aprotinin,
   Leu-15-Leu-17-Glu-52-aprotinin,
   Leu-15-Leu-17-Thr-52-aprotinin,
   Leu-15-Leu-17-Glu-39aprotinin,
   Leu-15-Leu-17-Glu-39-Glu-52-aprotinin, and
   Leu-15-Leu-17-Glu-39-Thr-52-aprotinin.

4. A peptide according to claim 5 further comprising methionine in position −1 and/or a leader peptide.

5. A pharmaceutical composition comprising an effective amount of a peptide according to claim 1 and a pharmaceutically acceptable diluent.

6. A peptide according to claim 2 further comprising methionine in position −1 and/or a leader peptide.

7. A pharmaceutical composition comprising an effective amount of a peptide according to claim 2 and a pharmaceutically acceptable diluent.

8. A peptide according to claim 3 further comprising methionine in position −1 and/or a leader peptide.

9. A pharmaceutical composition comprising an effective amount of a peptide according to claim 3 and a pharmaceutically acceptable diluent.

10. A peptide according to claim 1 produced by recombinant DNA technology.

* * * * *

UNITED STATES PATENT AND TRADEMARK OFFICE
CERTIFICATE OF CORRECTION

PATENT NO. : 5,118,668
DATED : June 2, 1992
INVENTOR(S) : Auerswald et al.

It is certified that error appears in the above-identified patent and that said Letters Patent is hereby corrected as shown below:

Col. 26, line 52   Delete " claim 5 " and substitute -- claim 1 --

Signed and Sealed this

Thirtieth Day of November, 1993

Attest:

BRUCE LEHMAN

Attesting Officer

Commissioner of Patents and Trademarks